(12) United States Patent
Sabb et al.

(10) Patent No.: US 7,271,163 B2
(45) Date of Patent: Sep. 18, 2007

(54) CYCLOPENTA[B][1,4]DIAZEPINO [6,7,1-HI]INDOLES AND DERIVATIVES

(75) Inventors: Annmarie L. Sabb, Pennington, NJ (US); Robert L. Vogel, Stratford, NJ (US); James A. Nelson, Washington Crossing, PA (US); Sharon J. Rosenzweig-Lipson, East Brunswick, NJ (US); Gregory S. Welmaker, Collegeville, PA (US); Joan E. Sabalski, Yardville, NJ (US)

(73) Assignee: Wyeth, Madison, NJ (US)

( * ) Notice: Subject to any disclaimer, the term of this patent is extended or adjusted under 35 U.S.C. 154(b) by 241 days.

(21) Appl. No.: 10/898,029

(22) Filed: Jul. 23, 2004

(65) Prior Publication Data

US 2005/0004101 A1     Jan. 6, 2005

Related U.S. Application Data

(63) Continuation of application No. 10/016,331, filed on Nov. 2, 2001, now Pat. No. 6,777,407.

(60) Provisional application No. 60/245,593, filed on Nov. 3, 2000.

(51) Int. Cl.
| A61K 31/55 | (2006.01) |
| A61P 25/00 | (2006.01) |
| A61P 25/24 | (2006.01) |
| C07D 243/00 | (2006.01) |

(52) U.S. Cl. ...................... 514/219; 540/555
(58) Field of Classification Search ............... 514/219; 540/555
See application file for complete search history.

(56) References Cited

U.S. PATENT DOCUMENTS

| 3,235,564 A | 2/1966 | Wagner ..................... 549/11 |
| 3,296,252 A | 1/1967 | Frey et al. .................. 540/493 |
| 3,329,676 A | 7/1967 | Bell et al. ................... 540/493 |
| 3,335,134 A | 8/1967 | Frey et al. .................. 540/493 |
| 3,417,101 A | 12/1968 | Bell et al. ..................... 549/27 |
| 3,466,274 A | 9/1969 | DeRidder ................... 540/556 |
| 3,714,149 A | 1/1973 | Hester ........................ 540/496 |
| 3,914,250 A | 10/1975 | Kim ........................... 260/315 |
| 4,997,831 A | 3/1991 | Bays et al. ............... 514/211.1 |
| 5,045,545 A | 9/1991 | Bays et al. .................. 514/284 |
| 5,834,454 A | 11/1998 | Kitano et al. ............... 514/183 |
| 6,414,144 B1 | 7/2002 | Welmaker et al. .......... 540/555 |
| 6,503,900 B2 | 1/2003 | Sabb et al. .................. 514/219 |
| 6,699,852 B2 | 3/2004 | Robichaud et al. ......... 514/183 |
| 6,720,316 B2 | 4/2004 | McWhorter, Jr. ........... 514/215 |
| 6,777,407 B2 * | 8/2004 | Sabb et al. .................. 514/219 |
| 2002/0055504 A1 | 5/2002 | Chan .......................... 514/219 |
| 2002/0058689 A1 | 5/2002 | Welmaker et al. .......... 514/411 |
| 2002/0062022 A1 | 5/2002 | Sabb et al. .................. 540/556 |
| 2002/0107242 A1 | 8/2002 | Sabb et al. .................. 514/219 |
| 2002/0119966 A1 | 8/2002 | Sabb et al. .................. 514/219 |
| 2002/0128261 A1 | 9/2002 | Sabb et al. .................. 514/219 |

FOREIGN PATENT DOCUMENTS

EP    0344015 A2    11/1989

(Continued)

OTHER PUBLICATIONS

S. Archer et al., J. Am. Chem. Soc., 79, 5783-5785 (1957).

(Continued)

*Primary Examiner*—Brenda Coleman
(74) *Attorney, Agent, or Firm*—Fitzpatrick, Cella, Harper & Scinto

(57) ABSTRACT

This invention provides compounds of the formulae:

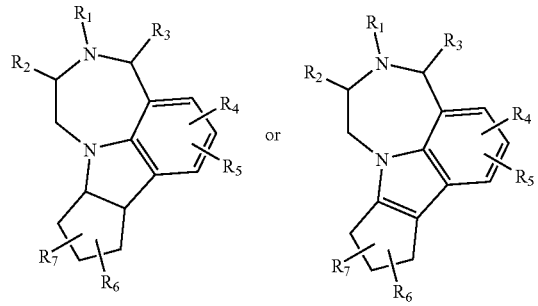

wherein:
$R_1$ is hydrogen, —C(O)CH$_3$ or alkyl of 1-6 carbon atoms;
$R_2$ and $R_3$ are each, independently, hydrogen, alkyl of 1-6 carbon atoms, cycloalkyl, alkoxy of 1-6 carbon atoms, —CH$_2$OH, fluoroalkyl, alkyl sulfonamide of 1-6 carbon atoms, alkyl amide of 1-6 carbon atoms, amino, alkylamino of 1-6 carbon atoms, dialkylamino of 1-6 carbon atoms per alkyl moiety, fluoroalkoxy of 1-6 carbon atoms, acyl of 2-7 carbon atoms, aryl, or aroyl;
$R_4$ and $R_5$ are each, independently, hydrogen, alkyl of 1-6 carbon atoms, alkoxy of 1-6 carbon atoms, halogen, fluoroalkyl, —CN, alkyl sulfonamide of 1-6 carbon atoms, alkyl amide of 1-6 carbon atoms, amino, alkylamino of 1-6 carbon atoms, dialkylamino of 1-6 carbon atoms per alkyl moiety, fluoroalkoxy of 1-6 carbon atoms, acyl of 2-7 carbon atoms, or aroyl;
$R_6$ and $R_7$ are each independently hydrogen, $C_1$-$C_6$ alkyl or cycloalkyl;
or a pharmaceutically acceptable salt thereof, as well as pharmaceutical compositions containing these compounds and methods for their use, including treatment of obsessive-compulsive disorder, panic disorder, depression, anxiety, generalized anxiety disorder, schizophrenia, migraine, sleep disorders, eating disorders, obesity, epilepsy, and spinal cord injury.

17 Claims, No Drawings

FOREIGN PATENT DOCUMENTS

| | | |
|---|---|---|
| EP | 0357417 A1 | 3/1990 |
| JP | 10-237073 | 9/1998 |
| SU | 930902 | 11/1982 |
| WO | WO90/15058 A1 | 12/1990 |
| WO | WO96/29316 | 9/1996 |
| WO | WO97/30999 A1 | 8/1997 |
| WO | WO97/31000 A1 | 8/1997 |
| WO | WO99/66934 A1 | 12/1999 |
| WO | WO99/67219 A1 | 12/1999 |
| WO | WO 00/35922 | 6/2000 |
| WO | WO 00/64899 A1 | 11/2000 |
| WO | WO 01/77002 A1 | 12/2000 |
| WO | WO 01/12603 A1 | 2/2001 |
| WO | WO 02/08186 | 1/2002 |
| WO | WO 02/36596 A2 | 5/2002 |
| WO | WO 02/42304 A2 | 5/2002 |
| WO | WO 02/059124 A2 | 8/2002 |
| WO | WO 02/059129 A2 | 8/2002 |

OTHER PUBLICATIONS

L. Zhang et al., Tetrahedron Letters, 36(46), 8387-8390 (1995).
G.E. Stokker, Tetrahedron Letters, 37(31), 5453-5456 (1996).
Cuadro et al., Synthetic Communications, 21(4), 535-544 (1991).
W. Perkin et al., J. Chem. Soc., 123, 3242-3247 (1923).
H. Booth et al., J. Chem. Soc., 158, 2302-2311 (1958).
Haerter et al., Chimia, 30(2), 50-52 (1976).
P.J. Cowen et al., Nature 376, 557 (Aug. 1995).
A.J. Robichaud et al., Annual Reports in Medicinal Chemistry, 35, 11-20 (2000).
D. Hoyer et al., Pharmacology & Experimental Therapeutics 46(2), 157-203 (1994).
L. Tecott et al., Nature, 374, 542-546 (Apr. 1995).
D.H. Kim, J. Heterocycl. Chem., 12, 1323-1324 (Dec. 1975).
M.J. Bishop et al., Expert Opin. Ther. Patents, 13(11), 1691-1705 (2003).
Shunji Naruto et al., Tetrahedron Letters, 39, 3399-3402 (1975).
A.N. Grinev et al., Chem. Heterocycl. Compd., 19(9), 959-961 (1983).
A.N. Grinev et al., Chem. Heterocycl. Compd., 19(12), 1312-1315 (1983).
E.V. Lamanova et al., Pharm. Chem., J., 23(2), 113-115 (1989).
D.H. Kim et al., Journal of Medicinal Chemistry, 20(2), 209-212 (1977).
L. Toscano et al., J. Heterocyclic Chem., 13, 475-480 (1976).
A. Katritzky et al., Synthesis, 10, 1487-1490 (1998).
F. Gatta et al., Edizione Scientifica, 30(8), 631-641 (1975).
W. Lopes et al., Journal of Brazilian Chemical Society, 4(1), 34-39 (1993).
Dong Han Kim, Synthesis of 1,2,3,4,8,9,10,11-Octahydro-[1,4] diazepino [6,5,4-jk]carbazole and Related Compounds, J. Heterocyclic Chem., vol. 13, pp. 1187-1192 (1976).
Jackson B. Hester, Jr., et al., Pyrrolo[3,2,1-jk][1,4]benzodiazepines and Pyrrolo[1,2,3-f][1,5]benzodiazepines Which Have Central Nervous System Activity, J. Med. Chem., vol. 13, No. 5, pp. 827-835 (1970).
J.L. Browning, et al., The Antipsychotic-Like Action of a 5-HT2c Agonist on conditioned Avoidance Behavior in Rats, Society for Neuroscience, Abstracts, vol. 25, part 2, p. 2075, abstract No. 830.12 (1999).
Gregory E. Martin, et al., Activity of Aromatic Substituted Phenylpiperazines Lacking Affinity for Dopamine Binding Sites in a Preclinical Test of Antipsychotic Efficacy, J. Med. Chem., vol. 32, pp. 1052-1056 (1989).

* cited by examiner

CYCLOPENTA[B][1,4]DIAZEPINO[6,7,1-HI]INDOLES AND DERIVATIVES

This application is a continuation of Ser. No. 10/016,331 filed Nov. 2, 2001, now U.S. Pat. No. 6,777,407 which claims the benefit under 35 U.S.C. §119(e) of provisional application No. 60/245,593, filed Nov. 3, 2000, the entire disclosure of which is hereby incorporated by reference.

The present invention relates to cyclopenta[b][1,4]diazepino[6,7,1-hi]indoles and derivatives thereof, which are serotonin 5-hydroxytryptamine $2_C$ ($5HT_{2C}$) receptor agonists useful for the treatment of central nervous system disorders including, but not limited to, obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J.) 147-210 (Wiley-Liss, New York, 1991).] The $5HT_{2C}$ receptor (formerly called the $5HT_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558-564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M., Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542-546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, and epilepsy.

The non-selective $5-HT_{2C}$ agonist, meta-chlorophenylpiperazine (m-CPP), has been shown to block conditioned avoidance responding (CAR) in the rat, an activity usually associated with antipsychotic activity in man [Martin, Gregory E.; Elgin, Jr., Robert J.; Mathiasen, Joanne R.; Davis, Coralie B.; Kesslick, James M.; Baldy, William J.; Shank, Richard P.; DiStefano, Deena L.; Fedde, Cynthia L.; Scott, Malcolm K. *J. Med. Chem.* 1989, 32, 1052-1056]. More recently, additional data suggests that $5-HT_{2C}$ agonism may produce an antipsychotic-like effect in the CAR model [Browning, J. L.; Young, K. A.; Hicks, P. B. Presented at the $29^{th}$ Annual Meeting of the Society for Neuroscience, Miami Beach, Fla., October 1999, Abstract 830.12].

U.S. Pat. No. 3,914,250 (Oct. 21, 1975) describes 1,4-diazepino[6,5,4-jk]carbazoles, having the structures below, as anticonvulsant agents.

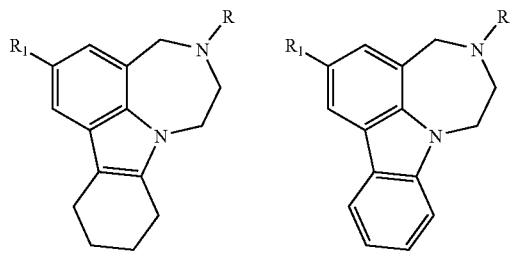

Pyrrolo[3,2,1-jk][1,4]benzodiazepines and 4,5-dihydro-pyrrolo[3,2,1-jk][1,4]-benzodiazepines have been described by Hester et al. (*J. Med. Chem.* 1970, 13, 827-835) to have central nervous system activity.

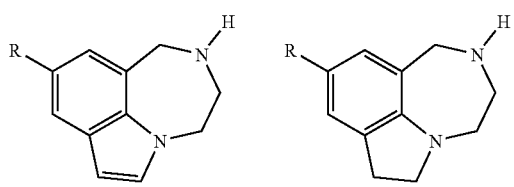

This invention provides cyclopenta[b][1,4]diazepino[6,7,1-hi]indoles and derivatives which bind to and activate $5HT_{2C}$ receptors in the CNS and are useful for the treatment of CNS disorders which can benefit from modulation of the $5HT_{2C}$ receptor.

DESCRIPTION OF THE INVENTION

This invention provides compounds of formula I having the structure:

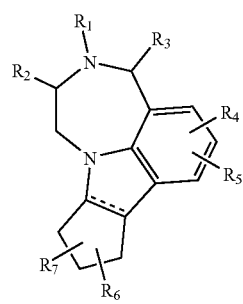

wherein:

$R_1$ is hydrogen, alkyl of 1-6 carbon atoms, acyl of 2-7 carbon atoms, aryl, aroyl or —C(O)R';

R' is alkyl of from 1 to 6 carbon atoms or aryl, preferably phenyl;

$R_2$ and $R_3$ are each, independently, hydrogen, alkyl of 1-6 carbon atoms, cycloalkyl, alkoxy of 1-6 carbon atoms, —$CH_2OH$, fluorinated alkyl of 1-6 carbon atoms, —NH—$SO_2$-alkyl of 1-6 carbon atoms, —$SO_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl, or aroyl;

$R_4$ and $R_5$ are each, independently, hydrogen, alkyl of 1-6 carbon atoms, alkoxy of 1-6 carbon atoms, halogen, fluorinated alkyl of 1-6 carbon atoms, —CN, —NH—$SO_2$-alkyl of 1-6 carbon atoms, —$SO_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, or aroyl;

$R_6$ and $R_7$ are each independently hydrogen, $C_1$-$C_6$ alkyl, cycloalkyl of 3 to 7 carbon atoms or —$CH_2$— (cycloalkyl of 3 to 7 carbon atoms);

the dashed line indicates an optional double bond;

or a pharmaceutically acceptable salt thereof.

In the definitions of $R_1$ and $R_2$ herein, the fluorinated alkyl and fluorinated alkoxy groups indicate the specified alkyl or alkoxy groups having any amount of fluorine substitution including, but not limited to, groups such as —$CHF_2$, —$CF_3$, —$C_2F_5$, —$OCF_3$, etc.

In the definitions of $R_2$ and $R_3$, the aryl groups are preferably phenyl, thiophenyl, benzyl, furanyl, pyrrolyl, pyridinyl or pyrimidinyl, most preferably phenyl or thiophenyl. In the definitions of $R_2$ and $R_3$ and $R_4$ and $R_5$, the aroyl groups are preferably phenoyl or thiophenoyl.

Two groups of compounds within this invention comprises compounds of the formulae:

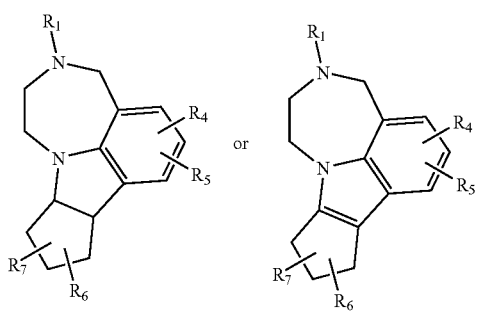

wherein $R_1$, $R_4$, $R_5$, $R_6$ and $R_7$ are as defined above, or a pharmaceutically acceptable salt thereof. A subset of this group of compounds comprise those in which R, is H or alkyl of from 1 to 6 carbon atoms, preferably H or —$CH_3$.

Another preferred group of the compounds are those of the formulae above wherein $R_1$ and $R_7$ are hydrogen and $R_4$, $R_5$, and $R_6$ are as defined above, or a pharmaceutically acceptable salt thereof. In a subset of these compounds, $R_1$, $R_4$, and $R_5$ are each hydrogen and $R_6$ and $R_7$ are as defined above, or a pharmaceutically acceptable salt thereof. In a further preferred subset $R_1$, $R_4$, $R_5$, and $R_6$ are hydrogen and $R_7$ is as defined above.

Another Set of Compounds within this Invention are those of the Formulae:

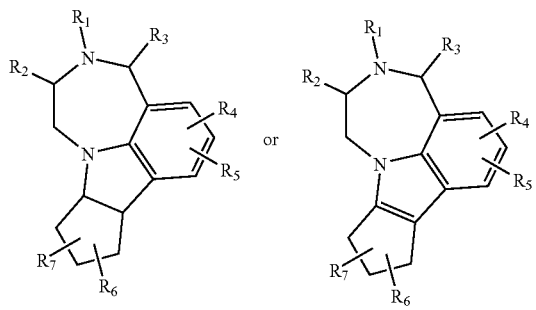

wherein:

$R_1$ is hydrogen, or alkyl of 1-6 carbon atoms;

$R_2$ and $R_3$ are each, independently, hydrogen, alkyl of 1-6 carbon atoms, cycloalkyl, alkoxy of 1-6 carbon atoms, —$CH_2OH$, or fluorinated alkyl of 1 to 6 carbon atoms, such as trifluoromethyl;

$R_4$ and $R_5$ are each, independently, hydrogen, alkyl of 1-6 carbon atoms, alkoxy of 1-6 carbon atoms, halogen, —CN, amino or fluorinated alkyl of 1 to 6 carbon atoms, such as trifluoromethyl;

$R_6$ and $R_7$ are each independently hydrogen or $C_1$-$C_6$ alkyl;

or a pharmaceutically acceptable salt thereof.

The $5HT_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

This invention also includes methods of utilizing the compounds herein in treatments or preventative regimens for treatment of central nervous system deficiencies associated with trauma, stroke, neurodegenerative diseases or toxic or infective CNS disorders including, but not limited to, encephalitis or meningitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

This invention includes methods for treating each of these conditions, the methods comprising administering to a mammal in need thereof a pharmaceutically or therapeutically effective amount of a compound of this invention, or a pharmaceutically acceptable salt thereof.

The compounds of this invention contain asymmetric carbon atoms and thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" includes both straight- and branched-chain saturated aliphatic hydrocarbon groups and cycloalkyl groups. Halogen is defined as Cl, Br, F, and I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

Preferred compounds of this invention are those in which $R_1$ is hydrogen. Especially preferred are compounds which are enantiomerically pure stereoisomers of compounds where $R_1$ is hydrogen and the pyrrole ring is reduced.

The compounds of this invention can be prepared according to the following scheme from commercially available starting materials or starting materials which can be prepared using literature procedures. Scheme 1 shows the preparation of representative compounds of this invention.

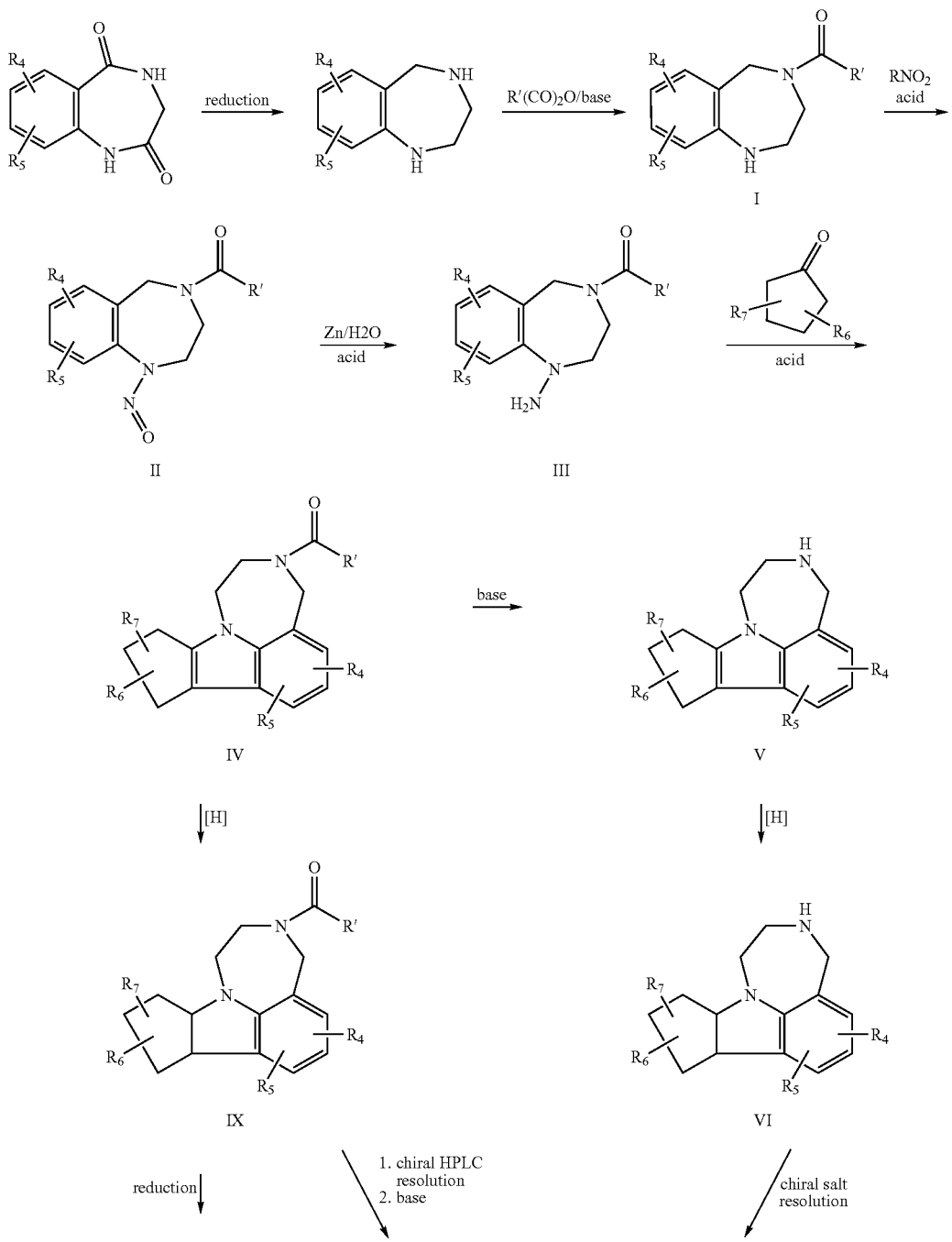

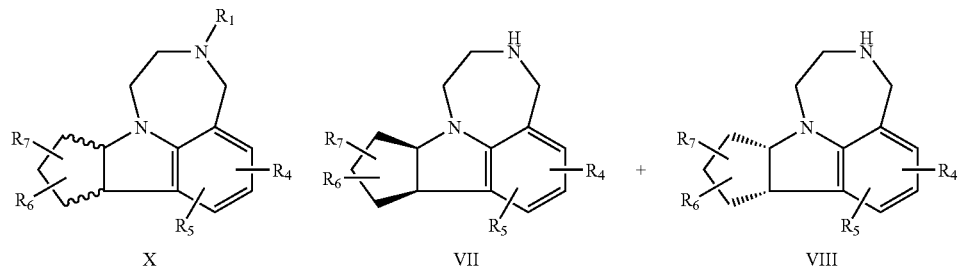

In Scheme 1, a substituted or unsubstituted benzodiazepinedione is reduced with a reducing agent, such as lithium aluminum hydride or a borane-tetrahydrofuran complex, to give a substituted or unsubstituted benzodiazepine. The basic nitrogen of the benzodiazepine is acylated with an acylating reagent, such as an acid anhydride, in the presence of a base, such as triethylamine, in an organic solvent, such as ether, to give intermediate I. Intermediate I is allowed to react with an organic or inorganic nitrosating agent, such as t-butyl nitrite or sodium nitrite, in the presence of an acid, such as acetic acid or hydrochloric acid, to give nitroso compounds II. The nitroso compounds are reduced to hydrazines III using a reducing agent, such as zinc powder in acetic acid and water. The hydrazines III are allowed to react with substituted or unsubstituted cyclopentanones in acid, such as acetic acid, to give the fused indoles IV. The fused indoles IV can be treated with a base, such as NaOH, in a polar solvent, such as water or an alcohol, to give the fused indoles V, which are products of this invention. In addition, fused indoles V can be reduced, such as by catalytic hydrogenation over a catalyst, such as palladium on charcoal, in an organic solvent, such as ethanol, in the presence of a trace of acid, such as trifluoroacetic acid, to give fused indolines VI which are products of this invention. Alternatively, fused indoles IV can be reduced, such as by catalytic hydrogenation over a catalyst, such as palladium on charcoal, in an organic solvent, such as ethanol, in the presence of a trace of an acid, such as trifluoroacetic acid, to give fused indolines IX. Fused indolines IX are racemic mixtures which can be resolved using chiral HPLC to give separated enantiomers which can then be treated with an inorganic base, such as NaOH in a polar solvent, such as water or methanol at elevated temperatures, such as 50-100° C., to remove the acyl group giving enantiomers VII and VIII which are products of this invention. Finally, fused indolines IX can be reduced with a reducing agent, such as a borane tetrahydrofuran complex, to give fused indolines X, which are compounds of this invention. Enantiomers VII and VIII can also be obtained by chiral salt resolution of racemic fused indolines VI using a resolving agent, such as benzoyltartaric acid, in an organic solvent, such as an alcohol.

Compounds of this invention were also prepared according to the following Scheme 2 from commercially available starting materials or starting materials which can be prepared using literature procedures.

Scheme 2

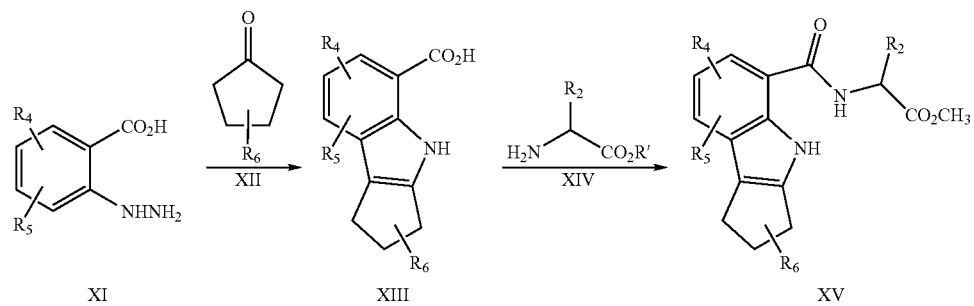

↓

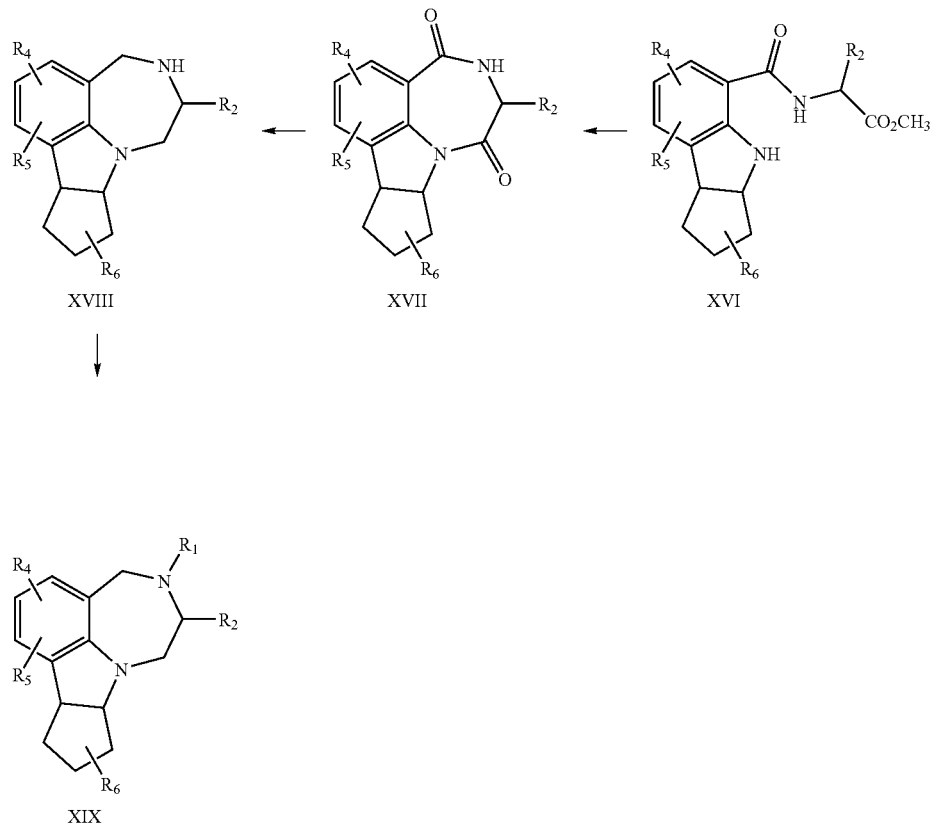

In Scheme 2, a 2-hydrazinobenzoic acid XI is allowed to react with a ketone XII under standard Fischer-indole conditions. The reaction is carried out in the presence of an acid, such as sulfuric acid or acetic acid, with or without a solvent, such as water or ethanol, at a temperature above ambient temperature, such as 30-150° C.

The resulting indole-carboxylic acid XIII is coupled with an amino acid ester XIV, such as L-alanine methyl ester, in the presence of peptide coupling reagents, such as 1-(3-dimethylaminopropyl)-3-ethylcarbodiimide hydrochloride (EDC) and 1-hydroxybenzotriazole hydrate (HOBt), and a base, such as diisopropylethylamine, in an inert organic solvent, such as dichloromethane.

The resulting indole-amide XV can be reduced to indoline-amide XVI by catalytic hydrogenation in the presence of a metal catalyst, such as 5% Pd/C or by a hydride source, such as triethylsilane or borane, in the presence of an acid, such as trifluoroacetic acid.

The indoline-amide XVI can be cyclized to the bislactam XVII by hydrolysis of the ester with a base, such as lithium hydroxide, and subsequent treatment with an acid, such as acetic acid.

The bislactam XVII can be reduced to the benzodiazepine XVIII, which are compounds of this invention, with a reducing agent, such as borane or lithium aluminum hydride, in the presence of an inert organic solvent, such as tetrahydrofuran.

When $R_1 \neq H$, reaction of benzodiazepine XVIII with an alkyl halide, such as methyl iodide, or an acyl halide, such as acetyl chloride, or an aroyl chloride, such as benzoyl chloride, gives XIX which are also compounds of this invention.

An alternative synthetic route to compounds of this class is depicted in Scheme 3. An arylhydrazine XX is allowed to react with a ketone XII under standard Fischer-indole conditions. The reaction is carried out in the presence of an acid, such as sulfuric acid or acetic acid, with or without a solvent, such as water or ethanol, at a temperature above ambient temperature, such as 30-150° C.

The resulting indole XXI can be reduced to indoline XXII by catalytic hydrogenation in the presence of a metal catalyst, such as 5% Pd/C or by a hydride source, such as triethylsilane or borane, in the presence of an acid, such as trifluoroacetic acid.

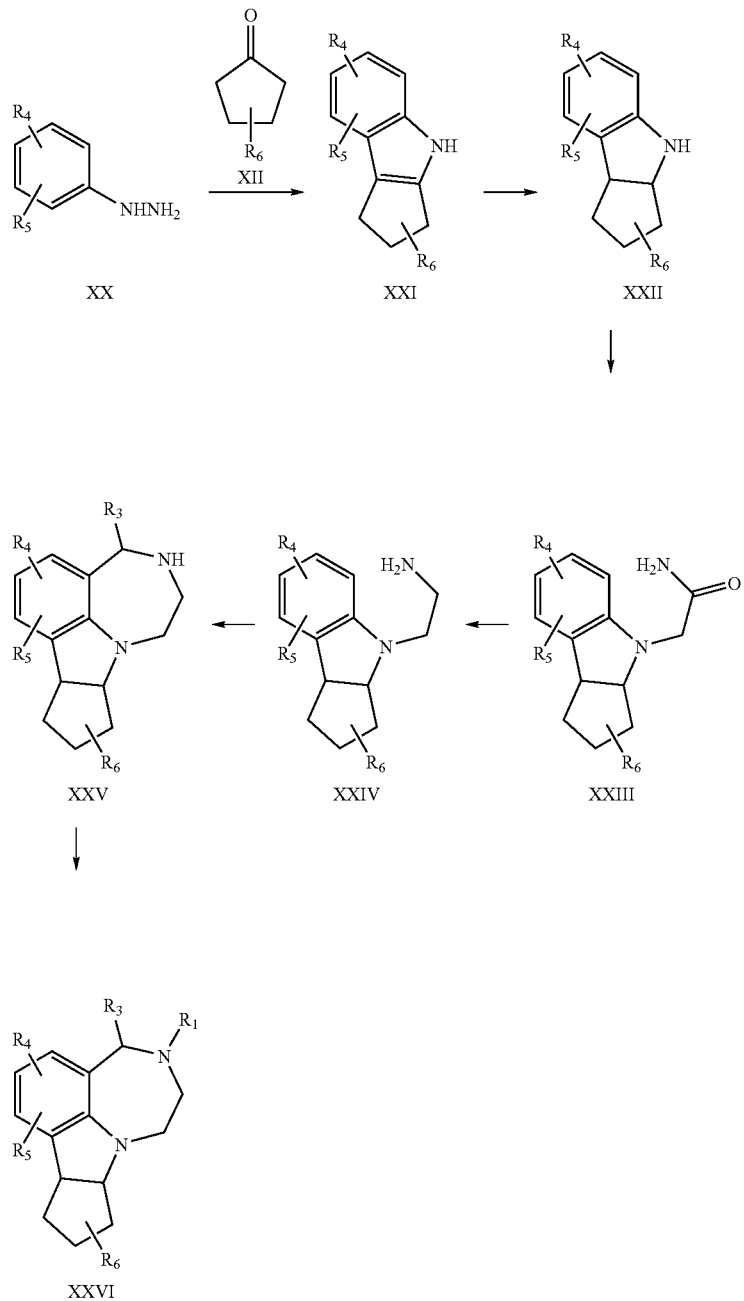

Scheme 3

The indoline XXII can be coupled with an appropriate electrophile, such as chloroacetamide (depicted), or a corresponding synthetic equivalent such as chloroacetonitrile, etc. in the presence of a base, such as diisopropylethylamine or potassium hydroxide, in a suitable solvent, such as DMF or DMSO to give the amide XXIII.

The amide XXIII can be reduced to the amine XXIV with a reducing agent, such as borane or lithium aluminum hydride, in the presence of an inert organic solvent, such as tetrahydrofuran.

The amine XXIV can be cyclized to the benzodiazepine XXV, which are compounds of this invention, by treatment with an aldehyde, such as formaldehyde or acetaldehyde, in the presence of an acid, such as trifluoroacetic acid, in a suitable solvent, such as ethanol, at room temperature or elevated temperatures.

When $R_1 \neq H$, reaction of benzodiazepine XXV with an alkyl halide, such as methyl iodide, or an acyl halide, such as acetyl chloride, or an aroyl chloride, such as benzoyl chloride, gives XXVI which are also compounds of this invention.

A further process for synthesizing compounds of this invention is presented in Scheme 4, wherein R, $R_1$, $R_2$, $R_3$ and $R_4$ are as defined above.

Scheme 4

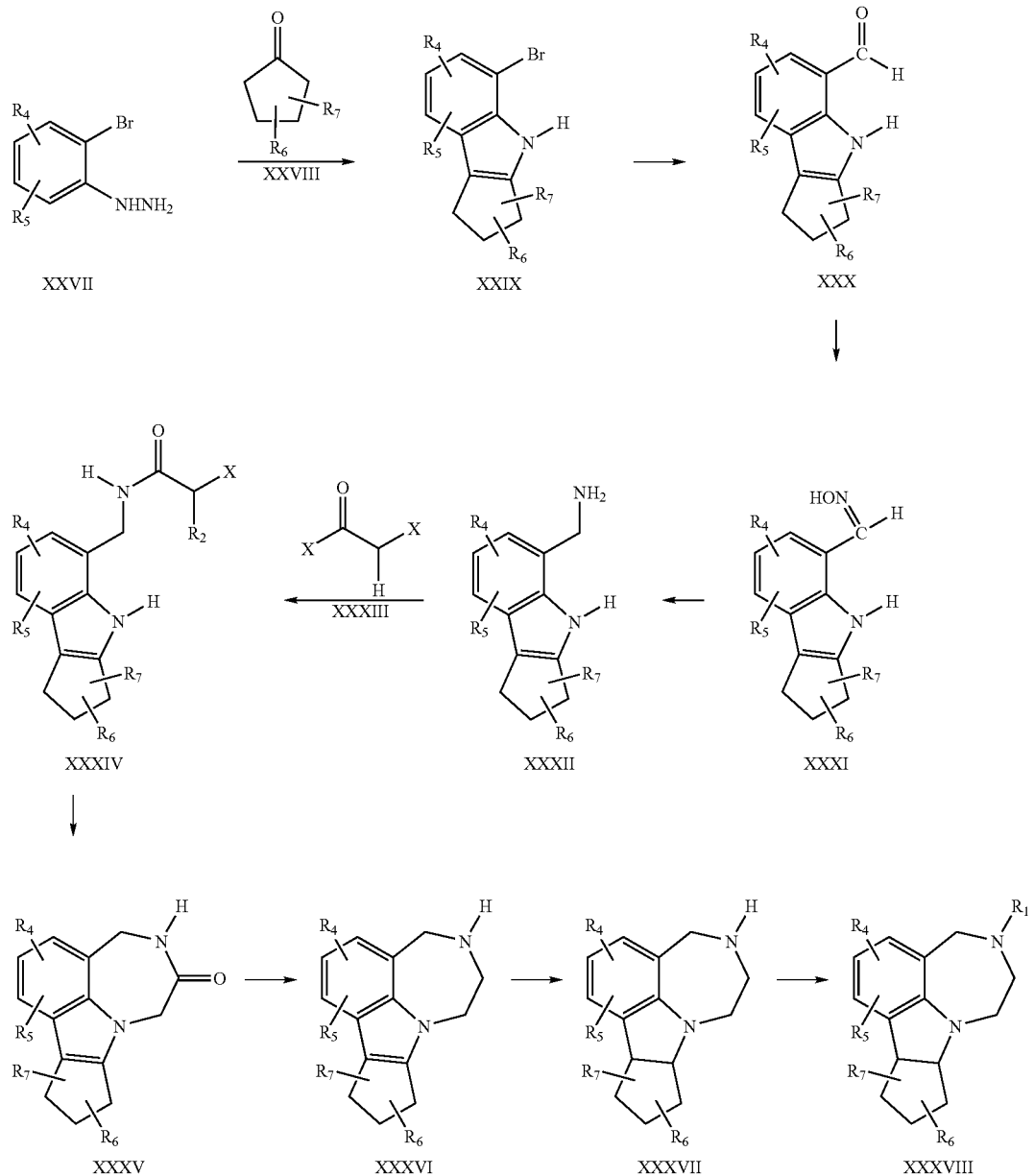

A 2-bromophenylhydrazine XXVII is allowed to react with a ketone XXVIII under standard Fisher-indole conditions. The reaction is carried out in the presence of an acid, such as sulfuric acid, acetic acid, or p-toluenesulfonic acid with or without a solvent, such as water, alkyl alcohol of 1-6 carbon atoms or dimethylforamide (DMF), at a temperature above ambient temperature, such as 30-150° C.

The resulting bromoindole XXIX may then be lithiated with reagent such as n-butyl lithium and formylated with formyl transfer agents such as DMF, N-formyl morpholine or ethyl formate in an acceptable solvent such as diethyl ether ($Et_2O$) or methyl t-butyl ether (MTBE) from −78° C. to ambient temperature.

The resulting indole aldehyde XXX is converted to an indole oxime XXXI using reagent such as hydroxylamine, N- or O-benzyl protected hydroxylamine in the presence of a suitable base such as pyridine or triethylamine (TEA) in a suitable solvent such as pyridine, water or tetrahydrofuran (THF).

The resulting indole oxime XXXI can be reduced to indole amine XXXII using a hydride source such as lithium aluminum hydride (LAH) or by catalytic hydrogenation in the presence of a metal catalyst such as palladium on carbon (Pd/C) or Raney nickel.

The resulting indole amine XXXII can be acylated with acid halide XXXIII, wherein X is an acceptable leaving group, preferably a halogen, such as chloroacetyl chloride in the presence of a base such as pyridine or TEA in a suitable solvent such as methylene chloride.

The resulting acyl indole XXXIV can be cyclized to indole amide XXXV in the presence of a suitable base such as sodium hydride (NaH), potassium hydride (KH) or lithium hydride (LiH) in the presence of a polar solvent such as THF, dimethylacetamide (DMA) or DMF.

Indole amide XXXV can be reduced to benzodiazepine indole XXXVI with reagents such as borane, LAH in a suitable solvent such as THF, $Et_2O$ or MTBE. Reduction of benzodiazepine indole XXXVII Reaction of benzodiazepine XXXVII with an alkyl halide of 1-6 carbon atoms such as methyl iodide, or an acyl halide, such as acetyl chloride, or an aroyl chloride, such as benzoyl chloride gives benzodiazepine XXXVIII.

The acylation steps of this invention are understood to include reactions of the appropriate compound with any acylating agent and reaction conditions known in the art. Useful in these steps are acylating agents include acid halides and esters or anhyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

This invention also provides a method for resolving the enantiomers of the compounds described herein. A method of resolving the (R,R) enantiomer of these compounds comprises the steps of:

a) dissolving about 1 equivalent of the racemic compound mixture of a product of this invention in a solubilizing amount of an alcohol resolving agent at a temperature of from about 50° C. to the reflux temperature for the alcohol, preferably between about 50° C. and 70° C., under an inert atmosphere, to create a resolving solution;

b) treating the resolving solution of step a) with from about 0.1 to about 0.35 equivalents of dibenzoyl-L-tartaric acid, preferably from about 0.15 equivalents to about 0.3 equivalents, more preferably from about 0.23 to about 0.27 equivalents, most preferably about 0.25 equivalents to precipitate the desired (R,R) enantiomer from the resolving solution as the corresponding tartaric acid salt form; and c) separating the desired enantiomer from the resolving solution through conventional means, such as filtration.

It will be understood that this process may be followed by additional steps of filtration and purification to enhance the purity and yield of the desired enantiomer product in question.

In step b) it is preferred that the temperature of the resolving solution be maintained at a temperature at or above about 50° C., preferably nearer to the reflux temperature of the alcohol in question.

The alcohol component of step a) may be comprise a single alcohol or a combination of two or more alcohols selected from those known in the art into which the compound in question can be dissolved. Among the preferred alcohols are the commercially available and relatively low boiling alcohols comprising 10 carbon atoms or less including methanol, ethanol, n-propanol, isopropanol, n-butanol, t-butanol, cyclohexanol, etc.

It will also be understood that the (S,S) enantiomer of the racemic mixture mentioned above could then be purified and collected from the remaining resolving solution described above after collection of the (R,R) tartaric acid salt.

This invention also provides an analogous method for resolving the (S,S) enantiomer from the racemic mixtures of compounds of this invention, the method comprising the steps a) through c) listed above, with dibenzoyl-D-tartaric acid being used in place of dibenzoyl-L-tartaric acid in step b). Comparably, the (R,R) enantiomer can be collected and purified by conventional means from the remaining solution after the tartaric acid salt form of the (S,S) enantiomer is precipitated and removed in this analogous method.

This invention also comprises pharmaceutical compositions and formulations utilizing the compounds described herein, comprising a pharmaceutically or therapeutically effective amount of one or more compounds of this invention, or a pharmaceutically acceptable salt thereof, and one or more pharmaceutically acceptable carriers or excipients.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

A pharmaceutically or therapeutically effective amount of the compounds herein is understood to comprise an amount of the compound(s) in question which will obtain at least a minimum of desired effect in preventing, treating, inhibiting or managing the symptoms or causes of the malady in question. More preferably, the amount will be the minimum needed to alleviate or remove the undesirable physiological consequences of the malady in question and inhibit or prevent their re-occurrence.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg-750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form. It will be understood that the dosage administered will be determined by a skilled medical professional taking into account the needs and physical characteristics of the recipient and the nature and extent of the malady to be treated or prevented.

The following provides the preparation of compounds representative of this invention.

EXAMPLE 1

1,2,3,4,9,10-Hexahydro-8H-cyclopenta[b]r[1,4]diazepino[6,7,1-hi]indole

A. 3-Acetyl-1,2,3,4,10-hexahydro-8H-cyclopenta[b][1,4]diazepino[6,7,1-hi]indole

4-Acetyl-2,3,4,5-tetrahydro-1H-1,4-benzodiazepine (8.92 g, 46.9 mmol) was dissolved in water (110 mL) and conc. HCl (6 mL). The solution was cooled in an ice bath and a solution of $NaNO_2$ (3.20 g) in water (10 mL) was added dropwise over 10 min with stirring. After stirring an additional 20 min the solution was extracted with methylene chloride. The organic phase was dried ($K_2CO_3$), filtered, and the volatiles were removed by evaporation under reduced pressure to give a residue. The residue was dissolved in glacial acetic acid (80 mL), cooled in an ice bath. Powdered zinc (23 g) was added portionwise over 10 min while keeping the reaction temperature below 30 C. Ater stirring for an additional 1.5 h, the reaction mixture was filtered through a pad of Celite. After washing the Celite with glacial acetic acid, cyclopentanone (20 g, 952 mmol, 20 equiv.) was added to the combined filtrates and the reaction mixture was heated (oil bath, 90-105° C.) for 2 h with stirring and then allowed to cool to room temperature and stir overnight.

Removal of the acetic acid by evaporation under reduced pressure, gave a residue which was partitioned between 2.5 N NaOH and ethyl acetate. The aqueous phase was extracted with additional ethyl acetate (3×) and the combined extracts were dried and evaporated under reduced pressure to give a residue. The residue was purified by column chromatography on silica gel eluting with 1-2% methanol in methylene chloride to give, 2.36 g (9.36 mmol.) of intermediate A, 3-acetyl-1,2,3,4,10-hexahydro-8H-cyclopenta[b][1,4]diazepino[6,7,1-hi]indole, as a viscous oil.

Intermediate A (2.34 g, 9.20 mmol) was dissolved in MeOH. The solution was diluted with 2.5N NaOH and solid NaOH pellets were added. The reaction mixture was placed in an oil bath at 95° C. for 6 h. then cooled to room temperature and stirred overnight. The volatiles were evaporated under reduced pressure and the residue was partitioned between water and ethyl acetate. The ethyl acetate was separated and evaporated and the residue was dissolved in methylene chloride and purified by chromatography on silica gel eluting with 2-5% methanol in methylene chloride to give the product of Example 1 as a light gray solid 1.56 g (80%), mp: 66-68° C.

Anal. Calcd. for $C_{14}H_{16}N_2$ Theory: % C, 79.21; % H, 7.60; % N, 13.20. Found: % C, 78.81; % H, 7.5; % N, 13.10

EXAMPLE 2

1,2,3,4,8,9,10,10a-octahydro-7bH-cyclopenta[b][1,4]diazepino[6,7,1-hi]indole

Method A.

The compound of Example 1 (1.56 g, 7.35 mmol) was dissolved in trifluoroacetic acid (53 mL) and cooled in an ice/water bath. 1.5 M $BH_3$ in THF (34 mL) was added dropwise slowly and stirred for an additional 15 min. after the addition was complete. Water was added slowly to quench the reaction followed by 2.5 N NaOH and 50% NaOH until the reaction mixture was basic (yellow color disappeared). After extraction with ethyl acetate (3×), the organic phase were combined and concentrated under reduced pressure to give a residue which was purified by chromatography on silica gel eluting with 3-10% MeOH in methylene chloride to give 600 mg (38%) of the product as a yellow solid: mp 64-68° C.

Anal. Calcd for $C_{14}H_{18}N_2.0.2H_2O$ Calcd: % C, 77.17; % H, 8.51; % N, 12.86. Found: % C, 77.13; % H, 8.18; % N, 12.61.

Method B.

3-Acetyl-1,2,3,4,8,9,10,10a-octahydro-7bH-cyclopenta[b][1,4]diazepino[6,7,1-hi]indole Intermediate A of Example 1 (2.07 g, 8.12 mmol) was dissolved in EtOH and hydrogenated over 10% Pd on carbon (0.25 g) in a Parr shaker at 55 lbs of hydrogen pressure. After 5 hrs, the reaction mixture was filtered through Celite to remove the catalyst and the filtrate was concentrated under reduced pressure to give a residue which was purified by chromatography on silica gel eluting with 0.3-2% MeOH in methylene chloride to give 1.84 g (87%) of 3-acetyl-1,2,3,4,8,9,10,10a-octahydro-7bH-cyclopenta[b][1,4]diazepino[6,7,1-hi]indole as a white solid, mp: 111-113° C.

Anal. Calcd for $C_{16}H_{20}N_2O+.20H_2O$ Theory: % C, 73.93; % H, 7.91; % N, 10.78. Found: % C, 74.05; % H, 7.91; % N, 10.79.

3-Acetyl-1,2,3,4,8,9, 10,10a-octahydro-7bH-cyclopenta[b][1,4]diazepino [6,7,1-hi]indole was dissolved in conc. HCl and heated with stirring in an oil bath (110° C.) for 12 hr. After cooling, the reaction mixture was made basic with 2.5N NaOH and 50% NaOH, extracted into methylene chloride, dried (MgSO$_4$), filtered and concentrated to give a residue. The residue was purified by chromatography on silica gel eluting with 1-20% MeOH in methylene chloride to give the product as a yellow solid, mp: 76-79° C.

EXAMPLE 3

The compound of Example 2 was chromatographed on a Chiral column eluting with MeOH containing 0.1% diethylamine.

Peak one was obtained as a yellow solid, mp: 51-54° C. and identified (7bS,10aS)-1,2,3,4,8,9,10,10a-octahydro-7bH-cyclopenta[b][1,4]diazepino[6,7,1-hi]indole Anal. Calcd for $C_{14}H_{18}N_2+0.20H_2O$ Theory: % C, 78.46;% H, 8.47;% N, 13.07. Found: % C, 77.09;% H, 8.50;% N, 12.72.

Peak two was obtained as a yellow solid, mp: 43-46° C. This peak was identified as a mixture of 92.3% (7bR,10aR)-1,2,3,4,8,9,10,10a-octahydro-7bH-cyclopenta-[b][1,4]diazepino[6,7,1-hi]indole and 7.7% of identified (7bS,10aS)-1,2,3,4,8,9,10,10a-octahydro-7bH-cyclopenta[b][1,4]diazepino[6,7,1-hi]indole

EXAMPLE 4

3-Acetyl-1,2,3,4,8,9,10,10a-octahydro-7bH-cyclopenta[b][1,4]diazepino[6,7,1-hi]indole was chromatographed on a Chiralcel AD chiral column (20×250 mm) eluting with 100% MeOH at room temperature, detection method: UV/VIS at 254 nm.

A. Peak one was obtained as a colorless viscous oil, identified as (7bS,10aS)-3-acetyl-1,2,3,4,8,9,10,10a-octahydro-7bH-cyclopenta[b][1,4]diazepino[6,7,1-hi]indole.

Anal. Calcd. for $C_{16}H_{20}N_2O+0.60H_2O$ Theory: % C, 71.93; % H, 8.00; % N, 10.49. Found: % C, 72.06; % H, 7.79; % N, 10.73. O.R.:[alpha]25/D=+118(19.2 mg/mL) MeOH)

(7bS,10aS)-3-Acetyl-1,2,3,4,8,9,10,10a-octahydro-7bH-cyclopenta[b][1,4]-diazepino[6,7,1-hi]indole was treated with solid NaOH in MeOH under reflux to give (7bS, 10aS)-1,2,3,4,8,9, 10,10a-octahydro-7bH-cyclopenta-[b][1, 4]diazepino-[6,7,1-hi]indole mp: 54-56° C.

O.R.: [alpha]25/D=+134.18 (10.359 mg/mL, MeOH)

B. Peak two was obtained as a colorless viscous oil, identified as (7bR,10aR)-3-acetyl-1,2,3,4,8,9,10,10a-octahydro-7bH-cyclopenta[b][1,4]diazepino[6,7,1-hi]indole Anal. Calcd. for $C_{16}H_{20}N_2O+.80H_2O$ Theory: % C, 70.98; % H, 8.04; % N, 10.35 Found: % C, 70.94; % H, 7.73; % N, 10.22 O.R.: [alpha]25/D=−132 (10.2 mg/mL MeOH)

(7bR, 10aR)-3-Acetyl-1,2,3,4,8,9, 10,10a-octahydro-7bH-cyclopenta-[b][1,4]diazepino[6,7,1-hi]indole was treated with solid NaOH in MeOH under reflux to give 7bR,10aR)-1,2,3,4,8,9,10,10a-octahydro-7bH-cyclopenta-[b][1,4]diazepino[6,7,1-hi]indole mp: 57-59° C.

Anal Calcd for $C_{14}H_{18}N_2$ Theory: % C, 77.81; % H, 8.49; % N, 12.96. Found: % C, 78.01; % H, 8.64; % N, 12.90.

EXAMPLE 5

(Chiral Salt Resolution of 1,2,3,4,8,9,10,10a-octahydro-7bH-cyclopenta[b][1,4]diazepino[6,7,1-hi]indole)

(7bR,10aR)-1,2,3,4,8,9,10,10a-octahydro-7bH-cyclopenta-[b][1,4]diazepino[6,7,1-hi]indole The compound of Example 2 (10.0 g, 46.7 mmol) was dissolved in isopropanol (500 mL) at 65-70° C. under nitrogen and dibenzoyl-L-tartaric acid (4.18 g, 11.7 mmol) was added all at one time. The resultant solids were slurried at 70-75° C. for two h, cooled to room temperature and stored at 10° C. for 12 h. The solids were filtered and washed twice with isopropanol (15 mL). The solids were reslurried in hot (80° C.) isopropanol (400 mL) for 1.5 h, cooled to room temperature and stored at 10° C. for 12 h. The solids were filtered and washed twice with isopropanol (15 mL) and air dried to give 7.3 g (79.9%) of the dibenzoyl-L-tartaric acid salt of the title compound as a white solid, mp: 163-5° C.

Anal. Calcd for $C_{14}H_{18}N_2.0.5$ $C_{18}H_{14}O_8.0.4$ $C_3H_8O$ Calcd: % C, 69.60; % H, 6.75; % N, 6.70. Found: % C, 69.80; % H, 6.73; % N, 6.58. O.R.: [alpha]25/D=−138.4 (1 mg/mL, MeOH)

The above tartrate salt (9.5 g, 12.1 mmol) was slurried in ethyl acetate (950 mL) and 1 N hydrochloric acid was added (25.0 mL, 25.0 mmol). The slurry was concentrated by atmospheric distillation (72-77° C.) to a volume of 275 mL, cooled to room temperature and stored overnight at 10° C. The solids were filtered and washed twice with ethyl acetate (20 mL) and air dried to give 5.7 g (92.8%) of the hydrochloride salt of the title compound as a white solid, mp 246-249° C. decomposed.

The HCl salt (5.6 g) was dissolved in ethanol (100 mL) at reflux. Upon cooling to room temperature, needle-like crystals formed. The mixture was stored overnight at 10° C. The solids were filtered, washed twice with ethanol (10 mL) and vacuum dried (57° C./0.1 mm) to give 3.8 g (67.8%) of white solid, mp 252-253° C. decomposed.

Anal. Calcd for $C_{14}H_{18}N_2.HCl$ Calcd: % C, 67.05; % H, 7.64; % N, 11.17. Found: % C, 66.74; % H, 7.54; % N, 11.09.

EXAMPLE 6

6-Methyl-1,2,3,4,9,10-hexahydro-8H-cyclopenta[b][1,4]diazepino[6,7,1-hi]indole By the same procedure as described for Example 1, 4-acetyl-7-methyl-2,3,4,5-tetrahydro-1,4-benzodiazepine, (3.64 g, 17.8 mmol) was converted to 246 mg of the title compound as a white solid, mp: 168-170° C.

Anal. Calcd for $C_{15}H_{18}N_2 \cdot 0.1H_2O$ Calcd: % C, 78.98; % H, 8.04; % N, 12.28. Found: % C, 78.87; % H, 8.15; % N, 12.04.

EXAMPLE 7

(2S)-rel-7bR,10aR)-2-Methyl-1,2,3,4,8,9,10,10a-octahydro-7bH-Cyclopenta[b][1,4]Diazepino[6,7,1-hi]Indole

A. 1,2,3,4-Tetrahydrocyclopenta[b]Indole-5-Carboxylic Acid

To a stirred solution of 2-hydrazinobenzoic acid hydrochloride (53 mmol, 10.0 g) and cyclopentanone (58 mmol, 4.9 g) in 1,4-dioxane (100 mL) was added dropwise concentrated $H_2SO_4$ (~18M, 63 mmol, 3.5 mL). The resulting solution was heated to reflux for 2 hours. $^1$H NMR analysis of a crude aliquot indicated complete reaction. The reaction was allowed to cool to room temperature and then concentrated to dryness to give a red solid which was used without further purification.

$^1$H NMR (DMSO-$d_6$, 300 MHz) δ 10.8(s, 1H), 7.6-7.0(m, 3H), 2.8(m, 4H), 2.4(m, 2H).

B. Ethyl (2S)-2-[(1,2,3,4-Tetrahydrocyclopenta[b]Indol-5-ylcarbonyl)Amino]-Propanoate To a stirred, cooled (0° C.) solution of crude 1,2,3,4-tetrahydrocyclopenta[b]indole-5-carboxylic acid (60 mmol, 12 g), L-alanine ethyl ester (72 mmol, 11 g), 1-[3-(dimethylamino)propyl]-3-ethylcarbodiimide hydrochloride (EDC) (72 mmol, 14 g), 1-hydroxybenzotriazole (HOBT) (72 mmol, 10 g) in $CH_2Cl_2$ (100 mL) was slowly added diisopropylethylamine (360 mmol, 46 g). The reaction mixture was stirred overnight while warming to room temperature. The reaction was concentrated in vacuo and the resulting oil was partitioned between water and ethyl acetate. The organic layer was washed with saturated aqueous $NH_4Cl$, $NaHCO_3$, and brine, dried over $MgSO_4$, filtered and concentrated to a brown oil. The crude material was purified by chromatography through silica gel (Biotage) eluting with 15% ethyl acetate-hexanes to afford a yellow oil (8.4 mmol, 2.5 g, 16% yield over 2 steps).

$^1$H NMR (DMSO-$d_6$, 300 MHz) δ 10.9(s, 1H), 8.74(d, 1H), 7.62(d, 1H), 7.48(d, 1H), 6.98(t, 1H), 4.47(t, 1H), 4.08(m, 2H), 2.75(m, 4H), 2.40(m, 2H), 1.42(d, 3H), 1.15(t, 3H).

C. Ethyl (2S)-2-[(1,2,3,3a,4,8b-Hexahydrocyclopenta[b]Indol-5-ylcarbonyl)-Amino]Propanoate A solution of ethyl (2S)-2-[(1,2,3,4-tetrahydrocyclopenta[b]indol-5-ylcarbonyl)amino]propanoate (8.4 mmol, 2.5 g) in ethanol (40 mL) was added to a mixture of 5% palladium on carbon (2 g) in ethanol (20 mL). Concentrated hydrochloric acid (10 mL) was added and the resulting mixture was hydrogenated at 45 psi for 4 hours. The reaction mixture was filtered through Celite. The filter bed was washed well with ethanol and the combined filtrates were concentrated. The resulting oil was partitioned between 1 N NaOH and ethyl acetate. The organic phase was dried over $MgSO_4$, filtered and concentrated to yield an oil (1.9 g, 6.1 mmol, 73% yield).

$^1$H NMR (DMSO-$d_6$, 300 MHz) δ 8.7(m, 1H), 7.63(m, 1H), 7.25(m, 1H), 6.85(m, 2H), 4.40(m, 2H), 4.10(m, 2H), 3.76(m, 1H), 1.90(m, 2H), 1.68(m, 3H), 1.38(d, 3H), 1.31(m, 1H), 1.16(t, 3H).

D. (2S)-2-[(1,2,3,3a,4,8b-Hexahydrocyclopenta[b]Indol-5-ylcarbonyl)Amino]-Propanoic Acid A 1 M aqueous lithium hydroxide solution (13 mmol, 13 mL) was added to a solution of ethyl (2S)-2-[(1,2,3,3a,4,8b-hexahydrocyclopenta[b]indol-5-ylcarbonyl)amino]propanoate (6.1 mmol, 1.9 g) in THF (50 mL). The reaction mixture was stirred at room temperature for 18 h. The reaction was concentrated in vacuo and diluted with 0.1 N HCl and ethyl acetate. The phases were separated and the organic phase was washed with water, dried over $MgSO_4$, filtered, and concentrated to give a yellow oil (1.6 g, 6.1 mmol, quantitative yield).

$^1$H NMR (DMSO-$d_6$, 300 MHz) δ 12.4(s, 1H), 8.21(d, 1H), 7.43(m, 1H), 7.01(d, 1H), 6.70(br s, 1H), 6.40(t, 1H), 4.35(m, 2H), 3.63(t, 1H), 1.88(m, 2H), 1.62(m, 4H), 1.30(d, 3H).

E. (2S)-2-Methyl-2,3,8,9,10,10a-Hexahydro-7bH-Cyclopenta[b][1,4]Diazepino-[6,7,1-hi]Indole-1,4-Dione A solution of (2S)-2-[(1,2,3,3a,4,8b-hexahydrocyclopenta[b]indol-5-ylcarbonyl)amino]propanoic acid (6.1 mmol, 1.6 g) was dissolved in acetic acid (50 mL) and heated to reflux for 18 h. The reaction was allowed to cool to room temperature and was concentrated to dryness. The crude material was purified by flash column chromatography (silica gel; 1:1 ethyl acetate-hexanes) to provide two diastereomers: less polar product (0.88 mmol, 0.23 g, 14%) and more polar product (0.18 mmol, 45 mg, 3%). The mixed fractions were also collected to provide another 3.9 mmol (1.0 g, 64%) of material.

Less Polar Product (A)

$^1$H NMR (DMSO-$d_6$, 300 MHz) δ 8.2(d, 1H), 7.61(m, 1H), 7.46(dd, 1H), 7.16(t, 1H), 4.86(dt, 1H), 3.87(m, 2H), 1.92(m, 2H), 1.75(m, 1H), 1.58(m, 2H), 1.26(d, 3H), 1.06(m, 1H).

(2S)-(rel-7bR,10aR)-2-Methyl-1,2,3,4,8,9,10,10a-Octahydro-7bH-Cyclopenta[b][1,4]Diazepino[6,7,1-hi]Indole A mixture of diastereomers of (2S)-2-methyl-2,3,8,9,10,10a-hexahydro-7bH-cyclopenta[b][1,4]diazepino[6,7,1-hi]indole-1,4-dione (3.9 mmol, 1.0 g) was suspended in 1 M $BH_3$.THF (15 mL) and heated to reflux for 18 h. After cooling to room temperature, the solution was quenched with methanol and concentrated. The resulting solid was suspended in 1 N NaOH and stirred at room temperature for 1 h. The aqueous phase was then extracted with chloroform and the combined extracts were dried over $MgSO_4$, filtered, and concentrated to give a yellow solid (3.5 mmol, 0.80 g, 90%). Flash chromatography through silica gel (gradient elution 5%-10% methanol-chloroform) afforded the two diastereomers. The less polar product was arbitrarily assigned the R,R configuration and the more polar product the S,S configuration.

Anal. Calcd. for $C_{15}H_{20}N_2 \cdot 1.5$ mol $H_2O$: C, 70.56; H, 9.08; N, 10.97. Found: C, 70.24; H, 9.58; N, 10.81. MS ((+))APCI, m/e (%)) 229(100, [M+H]$^+$). IR (solid ATR, cm$^{-1}$) 2960, 2880, 2310, 1460, 1440, 1210, 1160, 1120, 1090, 1070. $^1$H NMR (DMSO-d$_6$, 400 MHz) δ 7.32(t, J=7.56 Hz, 1H), 7.22(d, J=7.3 Hz, 1H), 7.12(d, J=7.3 Hz, 1H), 4.35(m, 1H), 4.07(m, 2H), 3.82(d, J=16.84 Hz, 1H), 3.62(m, 1H), 3.14(dd, J=8.54 Hz, 10.74 Hz, 1H), 3.0(m, 1H), 2.04-1.69(m, 4H), 1.51(m, 2H), 1.22(d, J=6.6 Hz, 4H). [α]$_D$+99 (c. 0.11, DMSO).

EXAMPLE 8

(2S)-(rel-7bS,10aS)-2-Methyl-1,2,3,4,8,9,10,10a-Octahydro-7bH-Cyclopenta[b][1,4]Diazepino[6,7,1-hi]Indole Following the procedure of method 7F, the more polar material provided the product which was assigned the S,S configuration.

Anal. Calcd. for $C_{15}H_{20}N_2 \cdot 1.1$ mol $H_2O$: C, 72.60; H, 9.02; N, 11.29. Found: C, 72.63; H, 8.80; N, 10.95. MS ((+)APCI, m/e (%)) 229(100, [M+H]$^+$). $^1$H NMR (DMSO-d$_6$, 400 MHz) δ 6.86(d, J=7.3 Hz, 1H), 6.73(d, J=7.3 Hz, 1H), 6.52(t, J=7.4 Hz, 1H), 3.95(m, 2H), 3.82(d, J=15.86 Hz, 1H), 3.61(m, 1H), 3.41(dd, J=3.17 Hz, 13.4 Hz, 2H), 3.21 (m, 1H), 2.83(dd, J=3.9 Hz, 13.2 Hz, 1H), 1.94(m, 1H), 1.77(m, 1H), 1.55(m, 4H), 1.15(d, J=6.6 Hz, 3H). [α]D+38 (c. 0.10, DMSO).

EXAMPLE 9

(2R)-rel-7bR,10aR)-2-Methyl-1,2,3,4,8,9,10,10a-Octahydro-7bH-Cyclopenta[b][1,4]Diazepino[6,7,1-hi]Indole A. Methyl (2R)-2-[(1,2,3,4-Tetrahydrocyclopenta[b]Indol-5-ylcarbonyl)Amino]-Propanoate Following the procedure of method 7B, employing D-alanine methyl ester (64 mmol, 8.9 g) afforded a yellow oil (4.9 mmol, 1.4 g).

$^1$H NMR (DMSO-d$_6$, 300 MHz) δ 10.8(s, 1H), 8.78(d, 1H), 7.61(d, 1H), 7.49(d, 1H), 7.0(t, 1H), 4.5(m, 1H), 3.63(s, 3H), 2.76(m, 4H), 2.42(m, 2H), 1.42(d, 3H).

B. Methyl (2R)-2-[(1,2,3,3a,4,8b-Hexahydrocyclopenta[b]Indol-5-ylcarbonyl)-Amino]Propanoate Following the procedure of method 7C, methyl (2R)-2-[(1,2,3,4-tetrahydrocyclopenta[b]indol-5-ylcarbonyl) amino]propanoate (4.9 mmol, 1.4 g) was hydrogenated using 5% Pd/C (1.5 g) and concentrated HCl (7 mL) in methanol (25 mL) to yield an oil (2.7 mmol, 0.77 g, 55%).

$^1$H NMR (DMSO-d$_6$, 300 MHz) δ 8.34(d, 1H), 7.44(d, 1H), 7.02(d, 1H), 6.70(s, 1H), 6.41(t, 1H), 4.39(m, 2H), 3.65(m, 1H), 3.60(s, 3H), 1.89(m, 1H), 1.61(m, 4H), 1.35(d, 3H), 1.29(m, 1H).

C. (2R)-2-[(1,2,3,3a,4,8b-Hexahydrocyclopenta[b]Indol-5-ylcarbonyl)Amino]-Propanoic Acid Following the procedure of method 7D, methyl (2R)-2-[(1,2,3,3a,4,8b-hexahydrocyclopenta[b]indol-5-ylcarbonyl) amino]propanoate (2.7 mmol, 0.77 g) was hydrolyzed to the acid using 1 M aqueous lithium hydroxide (5.9 mL) in THF (20 mL) to yield an orange oil which was used directly in the next step.

$^1$H NMR (DMSO-d$_6$, 300 MHz) δ 12.4(brs, 1H), 8.2(d, 1H), 7.43(d, 1H), 7.01(d, 1H), 6.9(br s, 1H), 6.4(t, 1H), 4.33(m, 2H), 3.62(t, 1H), 1.89(m, 2H), 1.61(m, 4H), 1.32(d, 3H).

D. (2R)-2-Methyl-2,3,8,9,10,10a-Hexahydro-7bH-Cyclopenta[b]-[1,4]Diazepino-[6,7,1-hi]Indole-1,4-Dione Following the procedure of method 7E, (2R)-2-[(1,2,3,3a,4,8b-hexahydrocyclopenta[b]indol-5-ylcarbonyl)amino] propanoic acid was cyclized by refluxing in acetic acid (50 mL). Purification by flash chromatography through silica gel (elution with 5% methanol-chloroform) provided each diastereomer: less polar product (1.5 mmol, 0.39 g, 56% over 2 steps) arbitrarily assigned as the R,R configuration and more polar product (0.47 mmol, 0.11 g, 17% over 2 steps) assigned as the S,S configuration.

Less Polar Product (A)

$^1$H NMR (DMSO-d$_6$, 300 MHz) δ 8.2(d, 1H), 7.62(d, 1H), 7.46(d, 1H), 7.16(t, 1H), 4.87(m, 1H), 3.88(m, 2H), 1.94(m, 3H), 1.76(m, 1H), 1.59(m, 2H), 1.28(d, 3H).

E. (2R)-(rel-7bR,10aR)-2-Methyl-1,2,3,4,8,9,10,10a-Octahydro-7bH-Cyclopenta[b][1,4] Diazepino [6,7,1-hi]Indole Following the procedure of method 7F, (2R)-(rel-7bR,10aR)-2-methyl-2,3,8,9,10,10a-hexahydro-7bH-cyclopenta[b]-[1,4]diazepino[6,7,1-hi]indole-1,4-dione (1.5 mmol, 0.39 g) was reduced with 1 M BH$_3$.THF (10 mL) to yield a yellow solid (0.47 mmol, 0.11 g, 31%).

Anal. Calcd. for $C_{15}H_{20}N_2 \cdot 0.15$ mol $H_2O$: C, 77.98; H, 8.86; N, 12.12. Found: C, 77.72; H, 9.03; N, 11.89. MS ((+)ESI, m/e(%)) 457(17, [2M+H]$^+$), 307(81, [M+H+DMSO]$^+$), 229(100, [M+H]$^+$). IR (solid ATR, cm$^{-1}$) 3240, 2950, 2870, 1590, 1460, 1350, 1290, 1270, 740. $^1$H NMR (DMSO-d$_6$, 400 MHz) δ 6.8(d, J=7.1 Hz, 1H), 6.65(d, J=7.1 Hz, 1H), 6.47(t, J=7.3 Hz, 1H), 3.94(m, 1H), 3.80, 3.71 (ABq, J$_{AB=16.1}$ Hz, 2H), 3.59(m, 1H), 3.35(dd, J=3.17 Hz, 12.93 Hz, 1H), 3.02(m, 1H), 2.75(dd, J=4.39 Hz, 12.93 Hz, 1H), 2.49(m, 1H), 1.94(m, 1H), 1.76(m, 1H), 1.56(m, 4H), 1.07(d, J=6.6 Hz, 3H). [α]$_D$–82 (c. 0.10, DMSO).

EXAMPLE 10

(2R)-(rel-7bS,10aS)-2-Methyl-1,2,3,4,8,9,10,10a-Octahydro-7bH-Cyclopenta[b ][1,4]Diazepino[6,7,1-hi]Indole Following the procedure of method 7F, (2R)-(rel-7bS,10aS)-2-methyl-2,3,8,9,10,10a-hexahydro-7bH-cyclopenta[b]-[1,4]diazepino[6,7,1-hi]indole-1,4-dione (0.47 mmol, 0.11 g) was reduced with 1 M BH$_3$.THF (8 mL) to yield the product (0.27 mmol, 61 mg, 57%).

MS ((+)APCI, m/e (%)) 457(20, [2M+H]$^+$), 229(100, [M+H]$^+$). $^1$H NMR (DMSO-d$_6$, 400 MHz) δ 6.85(d, J=7.08 Hz, 1H), 6.72(d, J=7.3 Hz, 1H), 6.52(t, J=7.3 Hz, 1H), 3.82(dd, J=5.6 Hz, 9.0 Hz, 1H), 3.79, 3.51(ABq, J$_{AB}$=15.1 Hz, 2H), 3.70(dt, J=2.9 Hz, 9.0 Hz, 1H), 3.28(m, 1H), 3.06(dd, J=2.1 Hz, 12.1 Hz, 1H), 2.78(m, 1H), 2.43(m, 1H), 1.92-1.30(m, 6H), 1.02(d, J=6.6 Hz, 3H).

EXAMPLE 11

(2R,7bS,10aS)-1,2,3,4,8,9,10,10a-Octahydro-7bH-Cyclopenta[b][1,4]Diazepino[6,7,1-hi]Indol-2-ylmethanol

A. Methyl (2S)-3-Hydroxy-2-[(1,2,3,4-Tetrahydrocyclopenta[b]Indol-5-ylcarbonyl)Amino]Propanoate Following the procedure of method 7B, employing L-serine methyl ester (64 mmol, 9.9 g) afforded a yellow solid (8.9 mmol, 2.7 g, 14%).

$^1$H NMR (DMSO-$d_6$, 300 MHz) δ 10.8(s, 1H), 8.51(d, 1H), 7.61(d, 1H), 7.51(d, 1H), 7.01(t, 1H), 5.08(m, 1H), 4.56(q, 1H), 3.82(d, 2H), 3.62(s, 3H), 2.76(m, 4H), 2.42(m, 2H).

B. Methyl (2S)-2-[(1,2,3,3a,4,8b-Hexahydrocyclopenta[b]Indol-5-ylcarbonyl)Amino]-3-Hydroxypropanoate Following the procedure of method 7C, methyl (2S)-3-hydroxy-2-[(1,2,3,4-tetrahydrocyclopenta[b]indol-5-ylcarbonyl)amino]propanoate (8.9 mmol, 2.7 g) was hydrogenated using 5% Pd/C (2 g) and concentrated HCl (10 mL) in methanol (25 mL) to yield the crude product (8.9 mmol, 2.7 g, quantitative).

$^1$H NMR (DMSO-$d_6$, 300 MHz) δ 8.3(d, 1H), 7.86(d, 1H), 7.34(d, 1H), 7.03(t, 1H), 5.80(br s, 2H), 4.45(m, 2H), 3.80(m, 2H), 3.61(s, 3H), 2.0-1.55(m, 6H).

B. (2S)-2-[(1,2,3,3a,4,8b-Hexahydrocyclopenta[b]Indol-5-ylcarbonyl]Amino}-3-Hydroxypropanoic Acid Following the procedure of method 7D, methyl (2S)-2-[(1,2,3,3a,4,8b-hexahydrocyclopenta[b]indol-5-ylcarbonyl)amino]-3-hydroxypropanoate (8.9 mmol, 2.7 g) was hydrolyzed to the acid using 1 M aqueous lithium hydroxide (40 mL) in THF (40 mL) to yield a red oil (1.5 mmol, 430 mg, 17%).

$^1$H NMR (DMSO-$d_6$, 300 MHz) δ 7.92(d, 1H), 7.40(d, 1H), 7.03(d, 1H), 6.43(t, 1H), 4.39(m, 2H), 3.63(br m, 4H), 2.0-1.2(m, 6H).

C. (2S)-2-(Hydroxymethyl)-2,3,8,9,10,10a-Hexahydro-7bH-Cyclopenta[b][1,4]-Diazepino[6,7,1-hi]Indole-1,4-Dione Following the procedure of method 7E, (2S)-2-[(1,2,3,3a,4,8b-hexahydrocyclopenta[b]indol-5-ylcarbonyl)amino]-3-hydroxypropanoic acid (1.5 mmol, 430 mg) was cyclized by refluxing in acetic acid (40 mL). Purification by flash chromatography through silica gel (elution with 5% methanol-chloroform) provided each diastereomer: less polar product (0.55 mmol, 0.15 g, 37%) arbitrarily assigned as the R,R configuration and more polar product (0.26 mmol, 0.070 g, 17%) assigned as the S,S configuration.

Less Polar Product (A)

$^1$H NMR (DMSO-$d_6$, 300 MHz) δ 8.44(d, 1H), 7.63(d, 1H), 7.48(d, 1H), 7.19(m, 1H), 4.88(m, 1H), 4.39(dd, 1H), 4.22(t, 1H), 4.07(m, 1H), 3.91(m, 1H), 2.0-1.5(m, 6H).

D. (2R)-(rel-7bS,10aS)-1,2,3,4,8,9,10,10a-Octahydro-7bH-Cyclopenta[b][1,4]-Diazepino[6,7,1-hi]Indol-2-ylmethanol Following the procedure of method 7F, (2S)-(rel-7bS,10aS)-2-hydroxymethyl-2,3,8,9,10,10a-hexahydro-7bH-cyclopenta[b]-[1,4]diazepino[6,7,1-hi]Indole-1,4-dione (0.26 mmol, 0.070 g) was reduced with 1 M BH$_3$·THF (1 mL) to yield a solid (0.17 mmol, 0.046 g, 65%).

MS ((+)APCI, m/e(%)) 323(35, [M+H+DMSO]$^+$, 245 (100, [M+H]$^+$). $^1$H NMR (DMSO-$d_6$, 400 MHz) δ 6.85(d, J=7.1 Hz, 1H), 6.73(d, J=7.3 Hz, 1H), 6.52(t, J=7.3 Hz, 1H), 4.70(m, 1H), 3.86, 3.50(ABq, J$_{AB}$=14.9 Hz, 2H), 3.85(m, 1H), 3.70(dt, J=2.9 Hz, 9.0 Hz, 1H), 3.35(m, 1H), 3.22(m, 2H), 2.64(m, 1H), 2.40(m, 1H), 1.90(m, 1H), 1.75(m, 1H), 1.60(m, 2H), 1.50(m, 1H), 1.40(m, 2H).

EXAMPLE 12 rel-(4S,7bS,10aS)-4-Methyl-1,2,3,4,8,9,10,10a-Octahydro-7bH-Cyclopenta[b][1,4]Diazepino[6,7,1-hi]Indole

A. 1,2,3,4-Tetrahydrocyclopenta[b]Indole

Concentrated sulfuric acid (~18 M, 35 mL) was added dropwise to a mixture of phenyl hydrazine (510 mmol, 50 mL) and cyclopentanone (45 mL, 510 mmol) in water (250 mL). The resulting mixture was heated to reflux for 30 min and then allowed to cool to room temperature. The liquid was decanted from the reaction mixture leaving a red, gummy solid. Hexanes (500-600 mL) was added to the flask and the mixture was heated to reflux. The yellow hexane solution was decanted hot from the mixture and placed in the freezer (crystallization begins immediately). More hexanes is added to the flask and the procedure repeated two more times using a total volume of 1500 mL of hexanes. After 1 h in the freezer, the solid was collected from the flasks and dried providing the known indole (410 mmol, 65 g, 80%).

Anal. Calcd. for C$_{11}$H$_{11}$N: C, 84.04; H, 7.05; N, 8.91 Found: C, 83.92; H, 7.12; N, 8.85

B. 1,2,3,3a,4,8b-Hexahydrocyclopenta[b]Indole

A mixture of 1,2,3,4-tetrahydrocyclopenta[b]indole (11 mmol, 1.8 g), 5% Pd/C (0.5 g), and concentrated hydrochloric acid (1.2 mL) was hydrogenated at 45 psi on a Parr shaker. After 3 h, the mixture was removed from the shaker and filtered through Celite. The solid bed was washed with methanol. The filtrate was concentrated. The crude oil was dissolved in 1 N HCl and washed with ether. The aqueous phase was treated with 2.5 N NaOH to pH>10 and then extracted with chloroform. The combined chloroform extracts were dried over MgSO$_4$, filtered and concentrated to give the crude indoline. The material was purified by flash column chromatography through silica gel (Biotage, elution with 10% ethyl acetate-hexanes) to give the known indoline (7.6 mmol, 1.2 g, 69%) as a clear oil.

Anal. Calcd. for C$_{11}$H$_{13}$N: C, 82.97; H, 8.23; N, 8.80 Found: C, 82.61; H, 8.35; N, 8.72

C. 2-(2,3,3a,8b-Tetrahydrocyclopenta[b]Indol-4(1H)-yl)Acetamide

To a stirred solution of 1,2,3,3a,4,8b-hexahydrocyclopenta[b]indole (130 mmol, 21 g) in DMF (50 mL) was added diisopropylethylamine (400 mmol, 70 mL) followed by 2-chloroacetamide (270 mmol, 25 g). The reaction mixture was heated to 100° C. for 18 h. The reaction was concentrated and the diluted with ethyl acetate and water. The phases were separated and the organic phase was washed with brine, dried over MgSO$_4$, filtered and concentrated. The crude material was purified by flash column chromatography through silica gel (elution with 60% ethyl acetate-hexanes) to afford a yellow solid (90 mmol, 20 g, 69%).

Anal. Calcd. for $C_{13}H_{16}N_2O$: C, 72.19; H, 7.46; N, 12.95. Found: C, 72.45; H, 7.57; N, 12.64. MS ((+)APCI, m/e(%)) 217(100, [M+H]$^+$). IR (solid ATR, cm$^{-1}$) 3450, 2930, 2870, 1680, 1480, 1150, 740. $^1$H NMR (DMSO-d$_6$, 400 MHz) δ 7.20(s, 1H), 7.05(s, 1H), 6.90(m, 2H), 6.48(dt, J=0.73 Hz, 7.3 Hz, 1H), 6.18(d, J=7.8 Hz, 1H), 4.22(m, 1H), 3.70, 3.58(ABq, J$_{AB}$=17.1 Hz, 2H), 3.64(m, 1H), 1.90(m, 1H), 1.78(m, 1H), 1.56(m, 3H), 1.40(m, 1H).

D. 2-(2,3,3a,8b-Tetrahydrocyclopenta[b]Indol-4 (1H)-yl)Ethylamine 2-(2,3,3a,8b-Tetrahydrocyclopenta[b]indol-4(1H-yl)acetamide (90 mmol, 20 g) was dissolved in 1 M BH$_3$.THF (200 mL) and heated to reflux for 18 h. The reaction mixture was allowed to cool to room temperature and then quenched slowly with methanol. The solution was concentrated, dissolved in methanol, and again concentrated. The resulting oil was diluted with ether and extracted twice with 1 N HCl. The aqueous phase was treated with 2.5 N NaOH to pH>10 and extracted with chloroform. The combined chloroform extracts were dried over MgSO$_4$, filtered and concentrated to provide a yellow oil which was used without further purification.

Anal. Calcd. for $C_{13}H_{18}N_2$.0.55 mol H$_2$O: C, 73.58; H, 9.07; N, 13.20. Found: C, 73.62; H, 8.80; N, 12.83. MS (EI, m/e(%)) 202(10, M$^+$), 172(100), 130(20). IR(film ATR, cm$^{-1}$) 2950, 2870, 1605, 1480, 1250(br), 730. $^1$H NMR (DMSO-d$_6$, 400 MHz) δ 6.89(dd, J=0.73 Hz, 7.3 Hz, 2H), 6.42(dt, J=0.73 Hz, 7.3 Hz, 1H), 6.29(d, J=7.6 Hz, 1H), 4.12(m, 1H), 3.62(dt, J=2.4 Hz, 9.0 Hz, 1H), 3.08(m, 2H), 2.65(m, 2H), 1.90(m, 1H), 1.75(m, 1H), 1.58(m, 3H), 1.43 (m, 1H).

E. rel-(4S,7bS,10aS)-4-Methyl-1,2,3,4,8,9,10,10a-Octahydro-7bH-Cyclopenta[b]-[1,4]Diazepino[6,7,1-hi]Indole 2-(2,3,3a,8b-tetrahydrocyclopenta[b]indol-4(1H)-yl) ethylamine (4.9 mmol, 1.0 g) was dissolved in ethanol (25 mL) at room temperature and trifluoroacetic acid (4.9 mmol, 380 μL) was added, followed by acetaldehyde (4.9 mmol, 280 μL). The reaction was heated to reflux overnight. The reaction vessel was cooled and then concentrated in vacuo. The resulting oil was partitioned between CHCl$_3$ and 1N NaOH. The aqueous phase was extracted again with CHCl$_3$. The combined organics were washed with 1N NaOH, dried over MgSO$_4$, filtered and concentrated in vacuo to yield a brown oil (23.8 mmol). The crude product was purified by flash chromatography (SiO$_2$) eluting with 10% MeOH/CHCl$_3$ to give the two racemic diastereomers.

Less Polar Product:

Rf 0.5 (A) 10% Et$_3$N/EtOAc MS ((+)APCI, m/e(%)) 229(100, [M+H]$^+$). IR (film ATR, cm$^{-1}$) 2940, 2860, 1460, 1430, 1330, 1300, 1230, 1070, 750. $^1$H NMR (DMSO-d$_6$, 400 MHz) δ 6.88(d, J=7.3 Hz, 1H), 6.81(d, J=7.8 Hz, 1H), 6.59(t, J=7.4 Hz, 1H), 3.87(m, 1H), 3.71(m, 1H), 3.45(q, J=6.7 Hz, 1H), 3.06(m, 2H), 2.80-2.67(m, 2H), 2.05(br m, 1H), 1.90(m, 1H), 1.75(m, 1H), 1.64(m, 1H), 1.52(m, 2H), 1.37 (m, 1H), 1.37(d, J=6.8 Hz, 3H).

EXAMPLE 13 rel-(4R,7bS,10aS)-4-Methyl-1,2,3,4,8,9,10,10a-Octahydro-7bH-Cyclopenta[b][1,4]Diazepino[6,7,1-hi]Indole The title product was prepared in Example 12E isolating the more polar product.

Rf 0.39 (B) 10% Et$_3$N/EtOAc MS ((+)APCI, m/e(%)) 229(100, [M+H]$^+$). IR (film ATR, cm$^{-1}$) 2950, 2930, 2860, 1600, 1460, 1430, 1320, 1230, 1050, 750. $^1$H NMR (DMSO-d$_6$, 400 MHz) δ6.81(d, J=7.1 Hz, 1H), 6.71(d, J=7.6 Hz, 1H), 6.52(t, J=7.3 Hz, 1H), 4.0(q, J=6.9 Hz, 1H), 3.82(dd, J=4.7 Hz, 8.6 Hz, 1H), 3.68(dt, J=2.7 Hz, 8.9 Hz, 1H), 3.05(m, 2H), 2.82-2.70(m, 2H), 2.3(brm, 1H), 1.88(m, 1H), 1.78(m, 1H), 1.64-1.48(m, 3H), 1.40(m, 1H), 1.17(d, J=7.1 Hz, 3H).

EXAMPLE NO. 14

9-methyl-1,2,3,4,8,9,10,10a-octahydro-7bH-cyclopenta[b][1,4]diazepino[6,7,1-hi]Indole

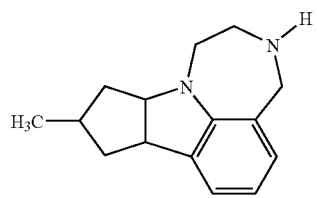

The title compound, which may also be named as 9-methyl-4,5,6,7,8,9,10,10a-octahydro-7bH-5,7a-diaza-benzo[cd]cyclopenta[a]azulene, was prepared according to the method of Example No. 2, above.

(for 1.5 HCl,).4H$_2$O mp: 244-250° C.) Theory: % C, 62.08; % H, 7.44; N, 9.65 Found: % C, 62.17; % H, &.33; % N, 9.25

EXAMPLE NO. 15

(7bR,9R,10aR)-9-methyl-1,2,3,4,8,9,10,10a-octahydro-7bH-cyclopenta[b][1,4]diazepino[6,7,1-hi]indole

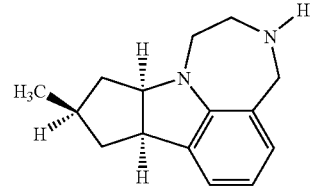

The title compound was prepared by the method described for Example Nos. 1 and 2, above, utilizing chiral 3-methyl-cyclopentanone, with purification of the final product by chiral HPLC.

(1 fumarate, 0.25H$_2$O, mp: 155-158° C.) Theory: % C, 65.41; % H, 7.08; % N, 8.02 Found: % C, 65.27; % H, 6.93; % N, 8.06

EXAMPLE NO. 16

9,9-dimethyl-1,2,3,4,8,9,10,10a-octahydro-7bH-cyclopenta[1,4]diazepino[6,7,1-hi]indole

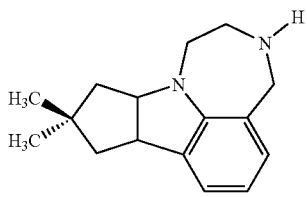

The title compound was prepared as described for the compound of Example No. 2 utilizing dimethylcyclopentanone. Anal. Consistent for 0.1H$_2$O Theory: % C, 66.68; % H, 7.33; % N, 7.78. Found % C, 66.41; % H, 7.11; % N, 7.61. (1 fumarate, 0.10H$_2$O, mp: 168-169° C.)

EXAMPLE 17

(7b,10aR)-9,9-dimethyl-1,2,3,4,8,9,10,10a-octahydro-7bH-cyclopenta[b][1,4]diazepino[6,7,1-hi]indole

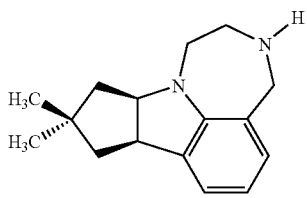

and

EXAMPLE 18

(7bS,10aS)-9,9-dimethyl-1,2,3,4,8,9,10,10a-octahydro-7bH-cyclopenta[b][1,4]diazepino[6,7,1-hi]indole

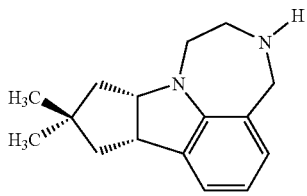

The compounds of Examples 17 and 18 were prepared according to the methods of Example No. 2 and separated by the methods of Example Nos. 3, 4 and 5. Example No 17 (1 fumarate, 0.75H$_2$O, mp:155-157° C.)

Theory: % C, 64.58; % H, 7.45; % N, 7.53 Found: % C, 64.80; % H, 7.71; % N, 7.17 Example No 18 (1 fumarate, 1H$_2$O, mp: 155-157° C.)

The ability of the compounds of this invention to act as 5HT$_{2C}$ agonists was established is several standard pharmacological test procedures; the procedures used and results obtained are provided below.

Test Procedures

5HT$_{2C}$ Receptor Binding Test Procedure

To evaluate high affinity for the 5HT$_{2C}$ receptor, a CHO (Chinese Hamster Ovary) cell line transfected with the cDNA expressing the human 5-hydroxytryptamine2$_C$ (h5HT2$_C$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 microliter (μl) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM CaCl$_2$ to give a tissue protein concentration of 1-2 mg per ml of suspension. The preparation membrane suspension (many times concentrated) was aliquoted in 1 ml volumes and stored at −70 C until used in subsequent binding experiments.

Binding measurements were performed in a 96 well microtiter plate format, in a total volume of 200 μl. To each well was added: 60 μl of incubation buffer made in 50 mM Tris.HCl buffer, pH 7.4 and containing 4 mM CaCl$_2$; 20 μl of [$^{125}$I] DOI (S.A., 2200 Ci/mmol, NEN Life Science).

The dissociation constant, KD of [$^{125}$I] DOI at the human serotonin 5HT$_{2C}$ receptor was 0.4 nM by saturation binding with increasing concentrations of [$^{125}$I] DOI. The reaction was initiated by the final addition of 100.0 μl of tissue suspension containing 50 μg of receptor protein. Nonspecific binding is measured in the presence of 1 μM unlabeled DOI added in 20.0 μl volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 μl Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following Ki's are provided for various refrence compounds:

Ki value and 95% confidence interval.

| | | |
|---|---|---|
| Ritanserin | 2.0 (1.3-3.1) nM | |
| Ketanserin | 94.8 (70.7-127.0) nM | |
| Mianserin | 2.7 (1.9-3.8) nM | |
| Clozapine | 23.2 (16.0-34.0) nM | |
| Methiothepin | 4.6 (4.0-6.0) nM | |
| Methysergide | 6.3 (4.6-8.6) nM | |
| Loxapine | 33.0 (24.0-47.0) nM | |
| mCPP | 6.5 (4.8-9.0) nM | |
| DOI | 6.2 (4.9-8.0) nM | |

Stimulation of [$^3$H] Inositol Monophosphate Production by 5HT$_{C2}$, Agonists.

CHO cells transfected with the cDNA expressing the human 5-HT$_{2C}$ receptor were cultured in Dulbecco's modified Eagle's medium (DMEM) supplemented with 10% fetal bovine serum and non-essential amino acids. Upon reaching confluence the cells were harvested using PBS/EDTA and plated in 24 well plates at an initial density of 2.5×10$^5$ cells per well. One (1) ml of maintenance medium containing 1 μCi/ml myo-[$^3$H] inositol was added to each well. After 48 hours labeling, the cells were washed once with 0.5 ml DMEM containing 25 mM HEPES and 10 mM LiCl, then preincubated with the medium for 30 min (antagonists were included in this period if tested). At the end of the preincubation, the medium was removed, the cells were then incubated with test compounds (in presence of antagonists if needed) for 30 min. The reaction was terminated by removal of the incubation solution and addition of 0.5 ml ice-cold 5% PCA, followed by 15 to 30 min incubation on ice. 200 μl of 0.5 M Tes/1.5 M K$_2$CO$_3$ was added to each well to neutralize to pH 7, and plates were left on ice for another 15 to 30 min to precipitate all salts. The liquid and solid phases were separated by centrifugation.

A portion (350 μl) of the upper aqueous phase was applied to Dowex AG-1×8 (formate form, 100-200 mesh) columns. The columns were then washed stepwise with 10 ml of water and 10 ml of 25 mM ammonium formate to remove free myo-[$^3$H]inositol and deacylated phosphoinositol, respectively. Finally 10 ml of 0.2 M ammonium formate solution was applied to the columns to elute [$^3$H] inositol monophosphate ([$^3$H] IP$_1$) directly into scintillation vials. Of this eluate, 1 ml was used to determine radioactivity by scintillation counting.

Agonist-stimulated levels of [$^3$H]inositol monophosphate (IP$_1$) is expressed as a percentage of the response observed with a maximally effective concentration of 5-HT (10 μM). A 3-parameter logistic function is used to generate estimate of EC$_{50}$/IC$_{50}$. Antagonists are tested in the presence of 10 μM 5-HT.

The following data are provided for various reference compounds:

| | | |
|---|---|---|
| 5-HT | 15.1 nM | EC$_{50}$ |
| mCPP | 46.8 nM | EC$_{50}$ |
| | 60% | E$_{MAX}$ (relative to 5-HT) |
| SB200646 | 286 nM | IC$_{50}$ (10 μM 5-HT as agonist) |

Effects of Compounds on Feeding Behavior in Rats

Eight (8) male Sprague-Dawley rats weighing 150-180 g were separated into individual cages and acclimated to a powdered diet for 2 weeks. During this period and throughout the test procedure, the food cup and the animals were weighed daily. Following the acclimation period, animals were fasted for 24 hours and then injected with either vehicle or one of 4 doses of the test compound. Food intake was assessed at 2 and 24 hours following compound administration. Compounds to be evaluated were injected 1-2× per week until all animals had received all doses of the test compound. The order of doses were chosen using to a modified Latin Square design. Additional studies may be conducted in satieted rats at the start of the dark cycle. Compounds were injected i.p, s.c. or p.o. At the end of the study effects of the test compound on food intake was evaluated using a repeated measures ANOVA. Data were collected were 2 hour food intake (g). Data were subjected to one-way ANOVA with posthoc t-tests to assess group differences. Where appropriate, ED50 values were calculated. The ED50 value is the dose that produces a 50% reduction in food intake during the test period.

Results

Results from In Vitro Test Procedures

| Compound | 5HT$_{2C}$ Affinity DOI/Agonist binding (Ki, nM) | 5HT$_{2C}$ % Emax (5HT, 100%) | Stimulation of IP3 (EC50, nM) |
|---|---|---|---|
| Example 1 | 97 | | |
| Example 2 | 18 | 110 | 136 |
| Example 4A | 2021 | 40 | 1254 |
| Example 4B | 10 | 100 | 76 |
| Example 6 | 985 | | |

Results from In Vivo 5HT$_{2C}$ Food Intake in Rats (24 hr Fast)

| Compound | Route of Admin. | ED50 (mg/kg) |
|---|---|---|
| Example 2 | ip | 8.05 |
| Example 4B | ip | 2.93 |

| Compound | 5-HT$_{2C}$ Affinity DOI/Agonist Binding (Ki, μM) |
|---|---|
| Example 7 | 6.0 |
| Example 8 | 5.9 |
| Example 9 | 0.91 |
| Example 10 | 4.3 |
| Example 11 | 1.9 |
| Example 12 | >5 |
| Example 13 | 0.31 |

What is claimed is:

1. A method of treating in a mammal a condition selected from bipolar disorders and psychosis, the method comprising administering to a mammal a pharmaceutically effective amount of a compound of formula I or a pharmaceutically acceptable salt thereof:

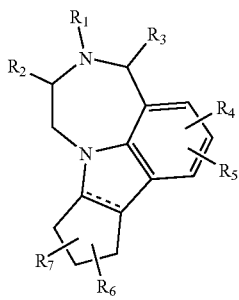

wherein:

$R_1$ is hydrogen, —C(O)CH$_3$ or alkyl of 1-6 carbon atoms;

$R_2$ and $R_3$ are each, independently, hydrogen, alkyl of 1-6 carbon atoms, cycloalkyl, alkoxy of 1-6 carbon atoms, —CH$_2$OH, fluorinated alkyl of 1-6 carbon atoms, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl, or aroyl;

$R_4$ and $R_5$ are each, independently, hydrogen, alkyl of 1-6 carbon atoms, alkoxy of 1-6 carbon atoms, halogen, fluorinated alkyl of 1-6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, or aroyl;

$R_6$ and $R_7$ are each independently hydrogen, $C_1$-$C_6$ alkyl, cycloalkyl of 3 to 7 carbon atoms or —CH$_2$—(cycloalkyl of 3 to 7 carbon atoms);

the dashed line indicates an optional double bond.

2. The method of claim 1 wherein the mammal is a human.

3. The method of claim 2 wherein the compound administered is at least one compound selected from

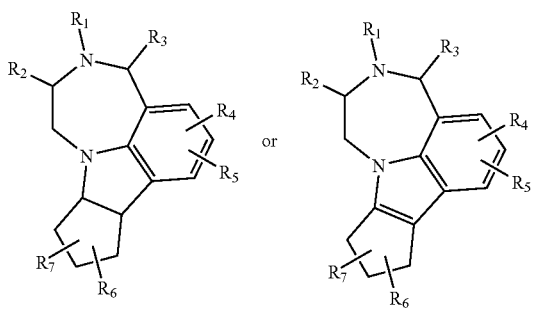

wherein:

$R_1$ is hydrogen, or alkyl of 1-6 carbon atoms;

$R_2$ and $R_3$ are each, independently, hydrogen or alkyl of 1-6 carbon atoms;

$R_4$ and $R_5$ are each, independently, hydrogen, alkyl of 1-6 carbon atoms, alkoxy of 1-6 carbon atoms, halogen, —CN, amino or fluorinated alkyl of 1 to 6 carbon atoms;

$R_6$ and $R_7$ are each independently hydrogen or $C_1$-$C_6$ alkyl;

or a pharmaceutically acceptable salt thereof.

4. The method of claim 2 wherein the compound administered is at least one compound selected from
   a) 1,2,3,4,9,10-hexahydro-8H-cyclopenta[b][1,4]diazepino[6,7,1-hi]indole;
   b) 1,2,3,4,8,9,10,10a-octahydro-7bH-cyclopenta[b][1,4]diazepino[6,7,1-hi]indole;
   c) 3-acetyl-1,2,3,4,8,9,10,10a-octahydro-7bH-cyclopenta[b][1,4]diazepino[6,7,1-hi]indole;
   d) 6-methyl-1,2,3,4,9,10-hexahydro-8H-cyclopenta[b][1,4]diazepino[6,7,1-hi]indole;
   e) 9-methyl-1,2,3,4,8,9,10,10a-octahydro-7bH-cyclopenta[b][1,4]diazepino[6,7,1-hi]indole;
   f) 9,9-dimethyl-1,2,3,4,8,9,10,10a-octahydro-7bH-cyclopenta[1,4]diazepino[6,7,1-hi]indole;

or a pharmaceutically acceptable salt thereof.

5. The method of claim 2 wherein the compound administered is at least one compound selected from:
   a) (7bR,10aR)-1,2,3,4,8,9,10,10a-octahydro-7bH-cyclopenta-[b][1,4]diazepino[6,7,1-hi]indole;
   b) (2S)-(rel-7bR,10aR)-2-methyl-1,2,3,4,8,9,10,10a-octahydro-7bH-cyclopenta[b][1,4]diazepino[6,7,1-hi]indole;
   c) (2S)-(rel-7bS,10aS)-2-methyl-1,2,3,4,8,9,10,10a-octahydro-7bH-cyclopenta[b][1,4]diazepino[6,7,1-hi]indole;
   d) (2R)-(rel-7bR,10aR)-2-methyl-1,2,3,4,8,9,10,10a-octahydro-7bH-cyclopenta[b][1,4]diazepino[6,7,1-hi]indole;
   e) (2R)-(rel-7bS,10aS)-2-methyl-1,2,3,4,8,9,10,10a-octahydro-7bH-cyclopenta[b][1,4]diazepino[6,7,1-hi]indole;
   f) (2R,7bS,10aS)-1,2,3,4,8,9,10,10a-octahydro-7bH-cyclopenta[b][1,4]diazepino[6,7,1-hi]indol-2-ylmethanol;
   g) rel-(4S,7bS,10aS)-4-methyl-1,2,3,4,8,9,10,10a-octahydro-7bH-cyclopenta[b][1,4]diazepino[6,7,1-hi]indole;
   h) rel-(4R,7bS,10aS)-4-methyl-1,2,3,4,8,9,10,10a-octahydro-7bH-cyclopenta[b][1,4]diazepino[6,7,1-hi]indole;
   i) (7bR,9R,10aR)-9-methyl-1,2,3,4,8,9,10,10a-octahydro-7bH-cyclopenta[b][1,4]diazepino[6,7,1-hi]indole;
   j) (7b,10aR)-9,9-dimethyl-1,2,3,4,8,9,10,10a-octahydro-7bH-cyclopenta[b][1,4]diazepino[6,7,1-hi]indole;
   k) (7bS,10aS)-9,9-dimethyl-1,2,3,4,8,9,10,10a-octahydro-7bH-cyclopenta[b][1,4]diazepino[6,7,1-hi]indole;

or a pharmaceutically acceptable salt thereof.

6. A method of treating in a mammal a condition selected from drug or alcohol addiction, social phobias, sexual dysfunction, sleep disorders, eating disorders, gastrointestinal disorders, diabetes, and premenstrual tension, the method comprising administering to a mammal a pharmaceutically effective amount of a compound of formula I or a pharmaceutically acceptable salt thereof:

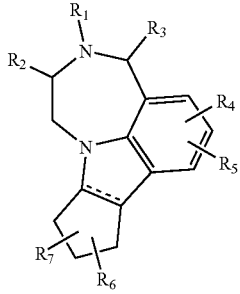

wherein:
R$_1$ is hydrogen, —C(O)CH$_3$ or alkyl of 1-6 carbon atoms;
R$_2$ and R$_3$ are each, independently, hydrogen, alkyl of 1-6 carbon atoms, cycloalkyl, alkoxy of 1-6 carbon atoms, —CH$_2$OH, fluorinated alkyl of 1-6 carbon atoms, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl, or aroyl;
R$_4$ and R$_5$ are each, independently, hydrogen, alkyl of 1-6 carbon atoms, alkoxy of 1-6 carbon atoms, halogen, fluorinated alkyl of 1-6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, or aroyl;
R$_6$ and R$_7$ are each independently hydrogen, C$_1$-C$_6$ alkyl, cycloalkyl of 3 to 7 carbon atoms or —CH$_2$— (cycloalkyl of 3 to 7 carbon atoms);
the dashed line indicates an optional double bond.

7. The method of claim 6 wherein the mammal is a human.

8. The method of claim 7 wherein the compound administered is at least one compound selected from

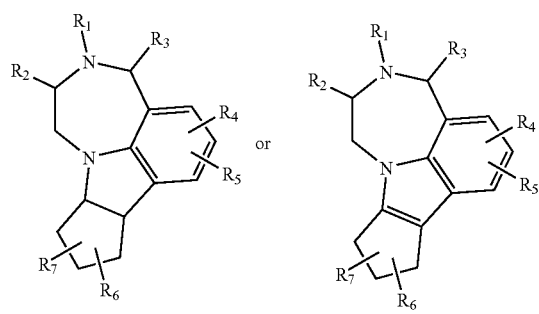

wherein:
R$_1$ is hydrogen, or alkyl of 1-6 carbon atoms;
R$_2$ and R$_3$ are each, independently, hydrogen or alkyl of 1-6 carbon atoms;

R$_4$ and R$_5$ are each, independently, hydrogen, alkyl of 1-6 carbon atoms, alkoxy of 1-6 carbon atoms, halogen, —CN, amino or fluorinated alkyl of 1 to 6 carbon atoms;
R$_6$ and R$_7$ are each independently hydrogen or C$_1$-C$_6$ alkyl;
or a pharmaceutically acceptable salt thereof.

9. The method of claim 7 wherein the compound administered is at least one compound selected from
a) 1,2,3,4,9,10-hexahydro-8H-cyclopenta[b][1,4]diazepino[6,7,1-hi]indole;
b) 1,2,3,4,8,9,10,10a-octahydro-7bH-cyclopenta[b][1,4]diazepino[6,7,1-hi]indole;
c) 3-acetyl-1,2,3,4,8,9,10,10a-octahydro-7bH-cyclopenta[b][1,4]diazepino[6,7,1-hi]indole;
d) 6-methyl-1,2,3,4,9,10-hexahydro-8H-cyclopenta[b][1,4]diazepino[6,7,1-hi]indole;
e) 9-methyl-1,2,3,4,8,9,10,10a-octahydro-7bH-cyclopenta[b][1,4]diazepino[6,7,1-hi]indole;
f) 9,9-dimethyl-1,2,3,4,8,9,10,10a-octahydro-7bH-cyclopenta[1,4]diazepino[6,7,1-hi]indole;
or a pharmaceutically acceptable salt thereof.

10. The method of claim 7 wherein the compound administered is at least one compound selected from:
a) (7bR,10aR)-1,2,3,4,8,9,10,10a-octahydro-7bH-cyclopenta-[b][1,4]diazepino[6,7,1-hi]indole;
b) (2S)-(rel-7bR,10aR)-2-methyl-1,2,3,4,8,9,10,10a-octahydro-7bH-cyclopenta[b][1,4]diazepino[6,7,1-hi]indole;
c) (2S)-(rel-7bS,10aS)-2-methyl-1,2,3,4,8,9,10,10a-octahydro-7bH-cyclopenta[b][1,4]diazepino[6,7,1-hi]indole;
d) (2R)-(rel-7bR,10aR)-2-methyl-1,2,3,4,8,9,10,10a-octahydro-7bH-cyclopenta[b][1,4]diazepino[6,7,1-hi]indole;
e) (2R)-(rel-7bS,10aS)-2-methyl-1,2,3,4,8,9,10,10a-octahydro-7bH-cyclopenta[b][1,4]diazepino[6,7,1-hi]indole;
f) (2R,7bS,10aS)-1,2,3,4,8,9,10,10a-octahydro-7bH-cyclopenta[b][1,4]diazepino[6,7,1-hi]indol-2-ylmethanol;
g) rel-(4S,7bS,10aS)-4-methyl-1,2,3,4,8,9,10,10a-octahydro-7bH-cyclopenta[b][1,4]diazepino[6,7,1-hi]indole;
h) rel-(4R,7bS,10aS)-4-methyl-1,2,3,4,8,9,10,10a-octahydro-7bH-cyclopenta[b][1,4]diazepino[6,7,1-hi]indole;
I) (7bR,9R,10aR)-9-methyl-1,2,3,4,8,9,10,10a-octahydro-7bH-cyclopenta[b][1,4]diazepino[6,7,1-hi]indole;
j) (7b,10aR)-9,9-dimethyl-1,2,3,4,8,9,10,10a-octahydro-7bH-cyclopenta[b][1,4]diazepino[6,7,1-hi]indole;
k) (7bS,10aS)-9,9-dimethyl-1,2,3,4,8,9,10,10a-octahydro-7bH-cyclopenta[b][1,4]diazepino[6,7,1-hi]indole;
or a pharmaceutically acceptable salt thereof.

11. The method of claim 7 wherein the condition is selected from sexual dysfunction.

12. The method of claim 7 wherein the condition is selected from diabetes.

13. A method of treating a mammal suffering from stroke, trauma or a spinal cord injury, the method comprising administering to a mammal a pharmaceutically effective amount of a compound of formula I or a pharmaceutically acceptable salt thereof:

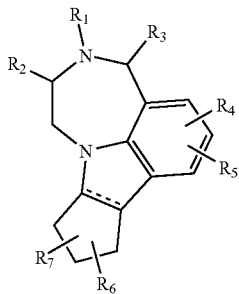

wherein:
R₁ is hydrogen, —C(O)CH₃ or alkyl of 1-6 carbon atoms;
R₂ and R₃ are each, independently, hydrogen, alkyl of 1-6 carbon atoms, cycloalkyl, alkoxy of 1-6 carbon atoms, —CH₂OH, fluorinated alkyl of 1-6 carbon atoms, —NH—SO₂-alkyl of 1-6 carbon atoms, —SO₂—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl, or aroyl;
R₄ and R₅ are each, independently, hydrogen, alkyl of 1-6 carbon atoms, alkoxy of 1-6 carbon atoms, halogen, fluorinated alkyl of 1-6 carbon atoms, —CN, —NH—SO₂-alkyl of 1-6 carbon atoms, —SO₂—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, or aroyl;
R₆ and R₇ are each independently hydrogen, C₁-C₆ alkyl, cycloalkyl of 3 to 7 carbon atoms or —CH₂— (cycloalkyl of 3 to 7 carbon atoms);
the dashed line indicates an optional double bond.

14. The method of claim 13 wherein the mammal is a human.

15. The method of claim 14 wherein the compound administered is at least one compound selected from

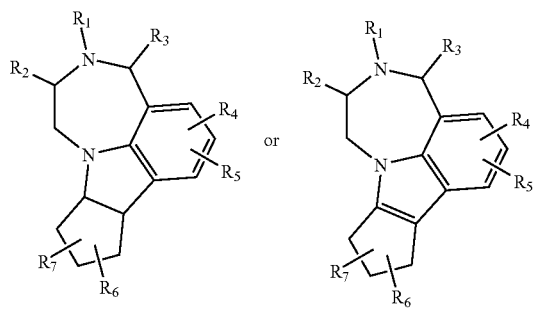

wherein:
R₁ is hydrogen, or alkyl of 1-6 carbon atoms;
R₂ and R₃ are each, independently, hydrogen or alkyl of 1-6 carbon atoms;
R₄ and R₅ are each, independently, hydrogen, alkyl of 1-6 carbon atoms, alkoxy of 1-6 carbon atoms, halogen, —CN, amino or fluorinated alkyl of 1 to 6 carbon atoms;
R₆ and R₇ are each independently hydrogen or C₁-C₆ alkyl;
or a pharmaceutically acceptable salt thereof.

16. The method of claim 14 wherein the compound administered is at least one compound selected from
 a) 1,2,3,4,9,10-hexahydro-8H-cyclopenta[b][1,4]diazepino[6,7,1-hi]indole;
 b) 1,2,3,4,8,9,10,10a-octahydro-7bH-cyclopenta[b][1,4]diazepino[6,7,1-hi]indole;
 c) 3-acetyl-1,2,3,4,8,9,10,10a-octahydro-7bH-cyclopenta[b][1,4]diazepino[6,7,1-hi]indole;
 d) 6-methyl-1,2,3,4,9,10-hexahydro-8H-cyclopenta[b][1,4]diazepino[6,7,1-hi]indole;
 e) 9-methyl-1,2,3,4,8,9,10,10a-octahydro-7bH-cyclopenta[b][1,4]diazepino[6,7,1-hi]indole;
 f) 9,9-dimethyl-1,2,3,4,8,9,10,10a-octahydro-7bH-cyclopenta[1,4]diazepino[6,7,1-hi]indole;
or a pharmaceutically acceptable salt thereof.

17. The method of claim 14 wherein the compound administered is at least one compound selected from:
 a) (7bR,10aR)-1,2,3,4,8,9,10,10a-octahydro-7bH-cyclopenta-[b][1,4]diazepino[6,7,1-hi]indole;
 b) (2S)-(rel-7bR,10aR)-2-methyl-1,2,3,4,8,9,10,10a-octahydro-7bH-cyclopenta[b][1,4]diazepino[6,7,1-hi]indole;
 c) (2S)-(rel-7bS,10aS)-2-methyl-1,2,3,4,8,9,10,10a-octahydro-7bH-cyclopenta[b][1,4]diazepino[6,7,1-hi]indole;
 d) (2R)-(rel-7bR,10aR)-2-methyl-1,2,3,4,8,9,10,10a-octahydro-7bH-cyclopenta[b][1,4]diazepino[6,7,1-hi]indole;
 e) (2R)-(rel-7bS,10aS)-2-methyl-1,2,3,4,8,9,10,10a-octahydro-7bH-cyclopenta[b][1,4]diazepino[6,7,1-hi]indole;
 f) (2R,7bS,10aS)-1,2,3,4,8,9,10,10a-octahydro-7bH-cyclopenta[b][1,4]diazepino[6,7,1-hi]indol-2-ylmethanol;
 g) rel-(4S,7bS,10aS)-4-methyl-1,2,3,4,8,9,10,10a-octahydro-7bH-cyclopenta[b][1,4]diazepino[6,7,1-hi]indole;
 h) rel-(4R,7bS,10aS)-4-methyl-1,2,3,4,8,9,10,10a-octahydro-7bH-cyclopenta[b][1,4]diazepino[6,7,1-hi]indole;
 I) (7bR,9R,10aR)-9-methyl-1,2,3,4,8,9,10,10a-octahydro-7bH-cyclopenta[b][1,4]diazepino[6,7,1-hi]indole;
 j) (7b,10aR)-9,9-dimethyl-1,2,3,4,8,9,10,10a-octahydro-7bH-cyclopenta[b][1,4]diazepino[6,7,1-hi]indole;
 k) (7bS,10aS)-9,9-dimethyl-1,2,3,4,8,9,10,10a-octahydro-7bH-cyclopenta[b][1,4]diazepino[6,7,1-hi]indole;
or a pharmaceutically acceptable salt thereof.

* * * * *